US011221339B2

(12) United States Patent
Varadarajan et al.

(10) Patent No.: US 11,221,339 B2
(45) Date of Patent: Jan. 11, 2022

(54) MAPPING PROTEIN BINDING SITES AND CONFORMATIONAL EPITOPES USING CYSTEINE LABELLING AND SURFACE DISPLAY LIBRARY

(71) Applicant: INDIAN INSTITUTE OF SCIENCE, Bangalore (IN)

(72) Inventors: Raghavan Varadarajan, Bangalore (IN); Tariq Ahmad Najar, Bangalore (IN); Rohini Datta, Bangalore (IN)

(73) Assignee: INDIAN INSTITUTE OF SCIENCE, Karnataka (IN)

( * ) Notice: Subject to any disclaimer, the term of this patent is extended or adjusted under 35 U.S.C. 154(b) by 122 days.

(21) Appl. No.: 16/467,229

(22) PCT Filed: Dec. 8, 2017

(86) PCT No.: PCT/IN2017/050581
§ 371 (c)(1),
(2) Date: Jun. 6, 2019

(87) PCT Pub. No.: WO2018/104967
PCT Pub. Date: Jun. 14, 2018

(65) Prior Publication Data
US 2020/0072850 A1    Mar. 5, 2020

(30) Foreign Application Priority Data

Dec. 8, 2016   (IN) .............................. 201641042053

(51) Int. Cl.
*C40B 30/04* (2006.01)
*G01N 33/68* (2006.01)
*C12N 15/10* (2006.01)
*C40B 40/02* (2006.01)

(52) U.S. Cl.
CPC ..... *G01N 33/6878* (2013.01); *C12N 15/1062* (2013.01); *C40B 30/04* (2013.01); *C40B 40/02* (2013.01); *G01N 33/6818* (2013.01); *G01N 33/6848* (2013.01); *G01N 33/6857* (2013.01)

(58) Field of Classification Search
None
See application file for complete search history.

(56) References Cited

U.S. PATENT DOCUMENTS

2003/0224448 A1* 12/2003 Harbury ............. G01N 33/6842
435/7.1

FOREIGN PATENT DOCUMENTS

WO    WO-2011143575 A2    11/2011

OTHER PUBLICATIONS

Bhanu et al. (Oct. 15, 2013) Journal of Bacteriology vol. 195 pp. 4709 to 4715.*

(Continued)

*Primary Examiner* — Christian C Boesen
(74) *Attorney, Agent, or Firm* — Marshall, Gerstein & Borun LLP

(57) ABSTRACT

The present disclosure provides a rapid, scalable, and high-throughput method of identifying the precise regions in a receptor protein which are involved in binding of a molecule of interest. The method of the instant disclosure is useful where the crystal structure of a protein of interest is not available. Also provided are surface display libraries, and methods of making the same.

17 Claims, 12 Drawing Sheets

(56) References Cited

OTHER PUBLICATIONS

Taslimi et al. (May 1, 2012) Journal of Molecular Biology vol. 418 pp. 367 to 378.*
De Jonge et al. (Jul. 2009) Molecular Cell vol. 35 pp. 154 to 163.*
International Search Report and Written Opinion for Application No. PCT/IN2017/050581, dated Mar. 19, 2018.
International Preliminary Report on Patentability for Application No. PCT/IN2017/050581, dated Jun. 11, 2019.
V. V. Ivanenkov et al., "Epitope mapping in cell surface proteins by site-directed masking: defining the structural elements of NTPDase3 inhibition by a monoclonal antibody", *Protein Engineering, Design & Selection*, vol. 23, No. 7, pp. 579-588 (2010).
Tariq Ahmad Najar et al., "Mapping Protein Binding Sites and Conformational Epitopes Using Cysteine Labeling and Yeast Surface Display", *Structure*, vol. 25, No. 3, pp. 395-406 (2017).

\* cited by examiner

MAPPING PROTEIN BINDING SITES AND CONFORMATIONAL EPITOPES USING CYSTEINE LABELLING AND SURFACE DISPLAY LIBRARY

FIELD OF INVENTION

The present disclosure relates to the field of mapping of protein-protein and protein-ligand binding interfaces binding sites using cysteine labeling and surface display libraries.

BACKGROUND OF THE INVENTION

In order to rationally design effective vaccines against bacterial and viral pathogens and to improve the efficacy of therapeutic antibodies, it is important to have rapid and reliable methods to map conformational epitopes. Such a methodology can be extended to map any macromolecular binding site. There are only a few methods to localize discontinuous epitopes such as three-dimensional structural determination of the antigen antibody complex by X-ray crystallography (Amit et al, 1986) or NMR (Rosen & Anglister, 2009; Zvi et al, 1995), alanine scanning (Cunningham & Wells, 1989; Weiss et al, 2000) and H/2H-exchange coupled to mass spectrometry (Carina et al, 2015; Pandit et al., 2012). However, such methods require highly purified, soluble antibody-protein complexes and are quite laborious. An alternate approach involves chemical tethering of the antigen to the solid surface via a cysteine residue, thus masking the area around the cysteine to prevent antibody binding to the antigen and hence define the location of the antibody epitope (Ivanenkov et al, 2010; Paus & Winter, 2006). A significant disadvantage of this technique is that one needs to express and purify all the cysteine mutants individually.

Yeast displaying a random mutagenesis library (Chao et al, 2004; Levy et al, 2007) a rationally designed mutant panel (Mata-Fink et al, 2013), or more recently site-saturation mutagenesis coupled to deep mutational scanning (Kowalsky et al, 2015; Van Blarcom et al., 2015) of an antigen has been used to map conformational epitopes. The main disadvantage of these methods is that similar to alanine scanning, mutating a residue to alanine or any other single residue will not always inhibit or prevent the binding of antibody to the antigen. Further, because a few hotspot residues contribute disproportionately to binding energetics, mutations of many residues in physical proximity to the antibody may be well tolerated and these epitopic residues will be missed. In addition, mutations at buried residues remote from the binding site can destabilize the protein and thus will also lead to loss of binding. Hence, if the structure of the antigen is not known it is difficult to determine if loss of binding is because of mutation in the epitope or in the protein interior. Thus, although saturation mutagenesis methodologies are powerful, they require considerable expertise and costs in library construction and analysis of deep sequencing data.

Controller of Cell Division or Death B (CcdB) is a globuler, dimeric protein with 101 residues per protomer, involved in the maintenance of the F plasmid in cells by a mechanism involving its binding to and poisoning of DNA Gyrase (Dao-thi, Van Melderen at el., 2005). This protein has been used to elucidate the method of the instant invention.

SUMMARY OF THE INVENTION

In an aspect of the present disclosure, there is provided a method of identifying binding sites of a molecule of interest to a receptor protein, said method comprising: (a) obtaining a display population, wherein said population comprises cells, phage or virus (hereafter collectively referred to for convenience as 'cells'), each member expressing on its surface mutant variants of the receptor protein, wherein said mutant variant has at least a single amino acid residue mutated to cysteine; (b) contacting a cysteine specific probe with said population, wherein said cysteine specific probe binds to the cysteine residue on the mutant variant; (c) contacting said molecule of interest with said population; and (d) detecting binding of molecule of interest to said mutant variant of the receptor protein, wherein lack of binding of the molecule of interest to the mutant variant is indicative that the corresponding amino acid residue in the receptor protein at the same position as that of the substituted cysteine in the mutated variant is involved in binding of the molecule of interest.

In an aspect of the present disclosure, there is provided a method of identifying binding sites of a molecule of interest to a receptor protein, said method comprising: (a) obtaining a display population, wherein said population comprises cells, phage or virus (hereafter collectively referred to for convenience as 'cells'), each member expressing on its surface mutant variants of the receptor protein, wherein said mutant variant has at least a single amino acid residue mutated to an amino acid residue selected from the group consisting of cysteine, alanine, serine, and any other amino acid; (b) contacting a cysteine specific probe with said population, wherein said cysteine specific probe binds to the cysteine residue on the mutant variant; (c) contacting said molecule of interest with said population; and (d) detecting binding of molecule of interest to said mutant variant of the receptor protein, wherein lack of binding of the molecule of interest to the mutant variant is indicative that the corresponding amino acid residue in the receptor protein at the same position as that of the substituted cysteine in the mutated variant is involved in binding of the molecule of interest.

In an aspect of the present disclosure, there is provided a yeast, phage, or lentiviral surface display library, wherein each member of the library has tethered to its surface a receptor protein mutant variant, wherein each variant has at least a single amino acid residue mutated to an amino acid residue selected from the group consisting of cysteine, alanine, serine, any other amino acid.

In an aspect of the present disclosure, there is provided a method of preparing a surface display library, wherein each member of the library has tethered to its surface a receptor protein mutant variant, wherein said receptor protein has no cysteine residues, each variant has a single mutation, and said mutation is a substituted cysteine, said method comprising: (a) obtaining a receptor protein; creating a population of receptor protein mutant variants, wherein each mutant variant contains a single amino acid residue mutated to cysteine; and (c) tethering mutant variants to yeast, mammalian, phage, or viral surface to obtain a surface display library.

In an aspect of the present disclosure, there is provided a method of preparing a surface display library, wherein each member of the library has tethered to its surface a receptor protein mutant variant, wherein said receptor protein has "n" number of cysteine residues involved in binding of molecule of interest, and in each mutant variant, the "n" number of cysteine residues of the receptor protein are substituted with alanine or serine, and further, an additional single substitution to cysteine is made at an amino acid position which is not any of the "n" number of cysteine residues in the receptor protein, said method comprising: (a) obtaining a receptor protein, wherein said receptor protein has "n" number of cysteine residues involved in binding of molecule of interest; (b) creating a population of receptor protein mutant variants, wherein in each mutant variant, the "n" number of cysteine residues of the receptor protein are substituted with alanine or serine, and further, an additional single substitution to cysteine is made at an amino acid position which is not any of the "n" number of cysteine residues in the receptor protein; and (c) tethering mutant variants to yeast, phage, lentiviral, viral or mammalian cell surface to obtain a surface display library.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF THE ACCOMPANYING DRAWINGS

The following figures form part of the present specification and are included to further illustrate aspects of the present disclosure. The disclosure may be better understood by reference to the figures in combination with the detailed description of the specific embodiments presented herein.

Figure 5:
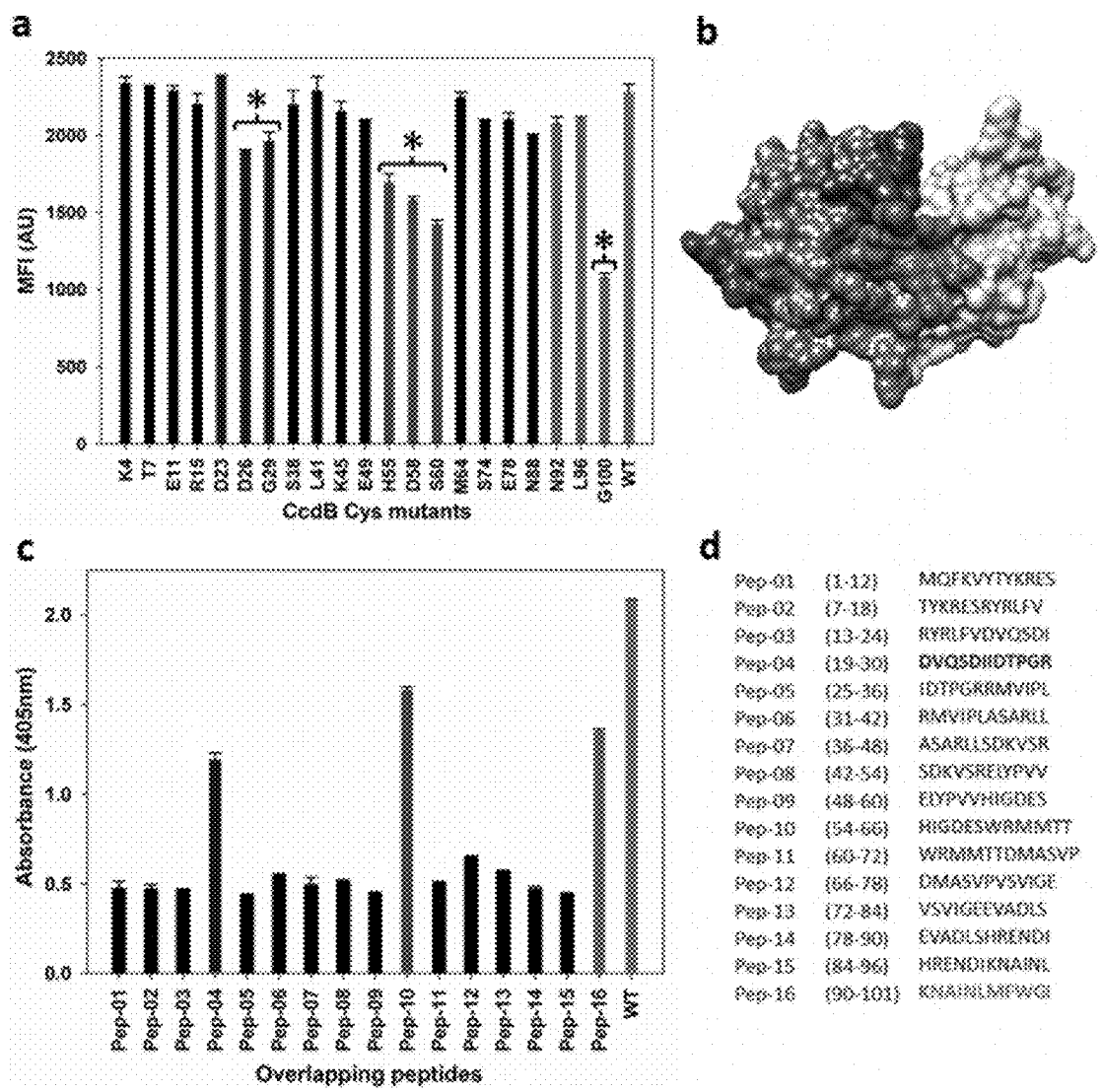
FIG. 5a depicts the binding of polyclonal sera to each yeast surface displayed labeled Cys mutant, in accordance with an embodiment of the present disclosure.
FIG. 5b depicts the immunodominant regions targeted by rabbit polyclonal sera in CcdB protein, in accordance with an embodiment of the present disclosure.

FIG. 5c, d depicts the binding of polyclonal sera to 16 biotinylated overlapping peptides of CcdB, in accordance with an embodiment of the present disclosure.

Figure 6:
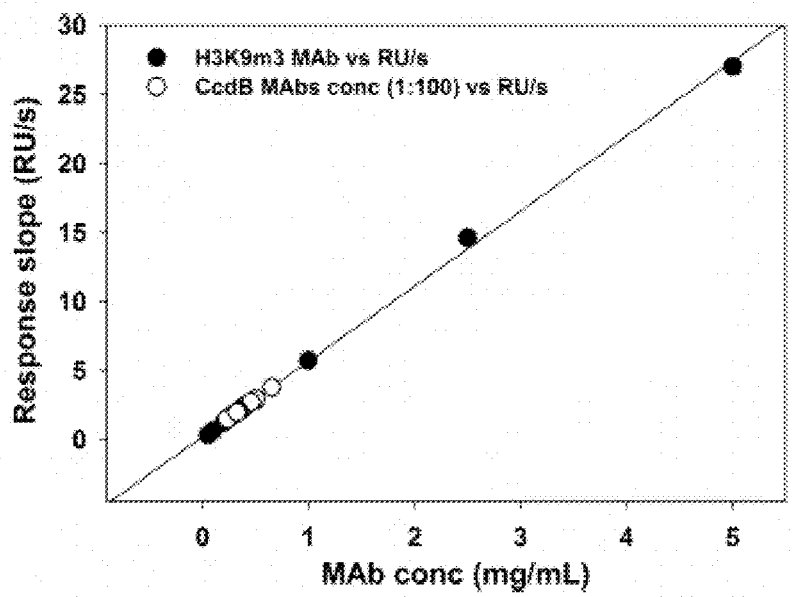

FIG. 6 depicts the determination of monoclonal antibody concentration in the culture supernatants by ProteOn XPR36, in accordance with an embodiment of the present disclosure.

Figure 7:
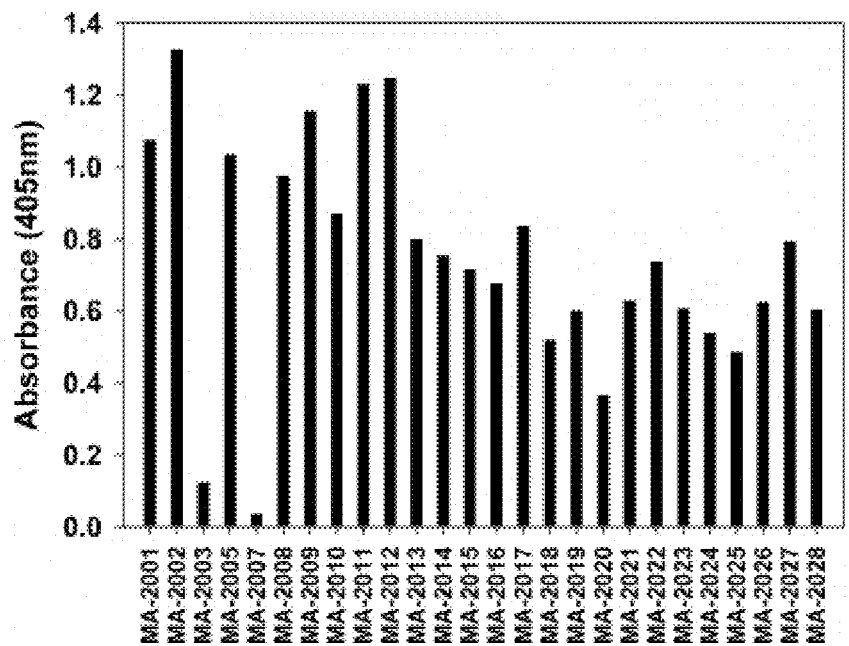

FIG. 7 depicts the monoclonal antibody binding to immobilized CcdB by ELISA, in accordance with an embodiment of the present disclosure.

Figure 8:
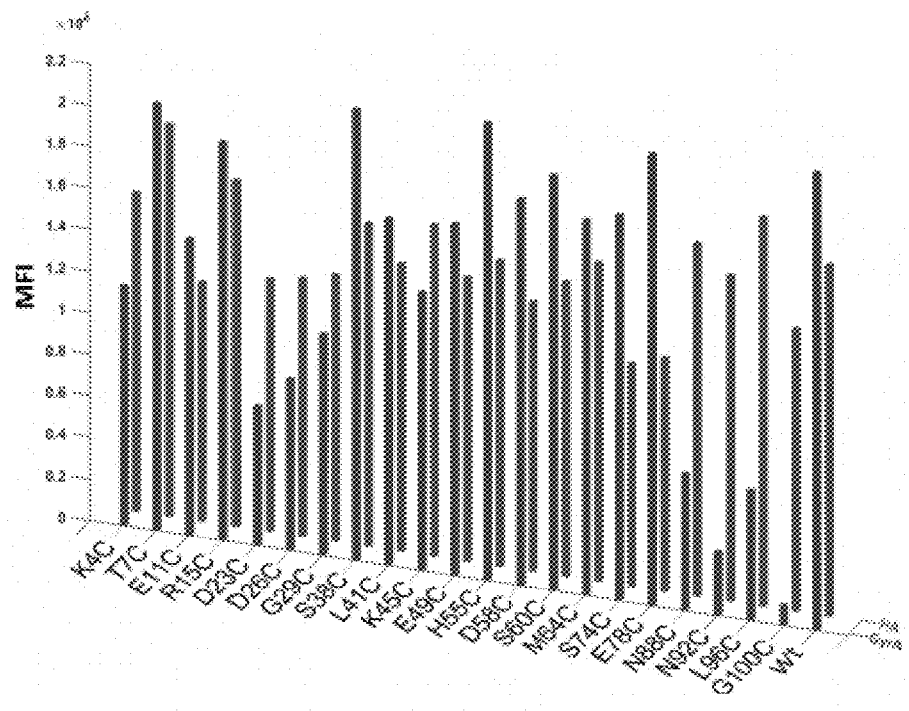

FIG. 8 depicts the binding of GyrA-14 and anti-HA antibody to the displayed unlabeled single cysteine mutants monitored by flow cytometry, in accordance with an embodiment of the present disclosure.

Figure 9:
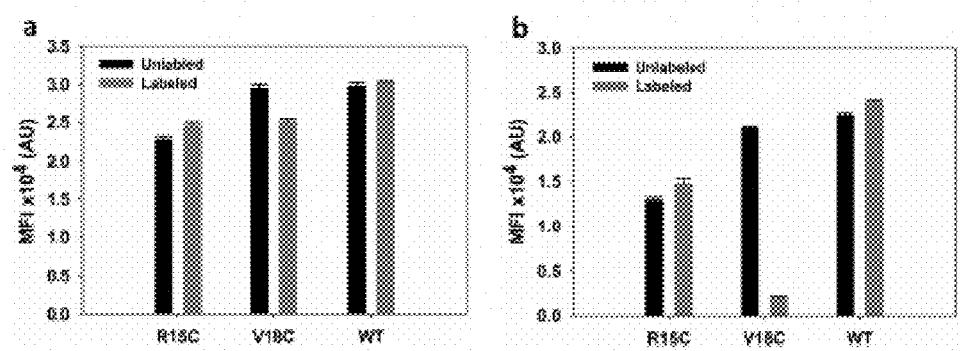

FIG. 9a depicts the labeling of exposed and buried residues of GyrA-14 in the absence of denaturant, in accordance with an embodiment of the present disclosure.

FIG. 9b depicts the labeling of exposed and buried residues of GyrA-14 in the presence of denaturant, in accordance with an embodiment of the present disclosure.

Figure 10:
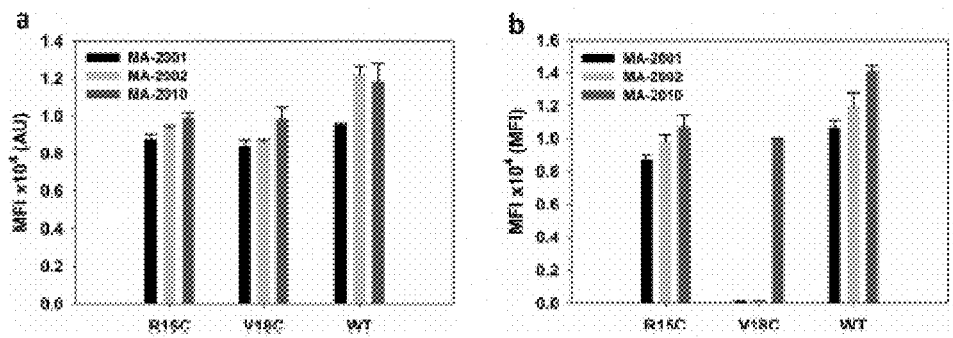

FIG. 10a depicts the binding of conformation specific antibody (MA-2001/2/10) to cysteine mutants labeled under native conditions, in accordance with an embodiment of the present disclosure.

FIG. 10b depicts the binding of conformation specific antibody (MA-2001/2/10) to cysteine mutants labeled under denaturing conditions, in accordance with an embodiment of the present disclosure.

FIG. 11a depicts the pictorial representation of the 16, 12-mer (with 6 amino acid overlap) designed from CcdB, in accordance with an embodiment of the present disclosure.

FIG. 11b depicts the amino acid sequence of the overlapping peptides, in accordance with an embodiment of the present disclosure.

FIG. 11c depicts the binding of MA-2001, MA2002, and MA-2010 against a panel of overlapping peptides derived from CcdB, in accordance with an embodiment of the present disclosure.

Figure 12:
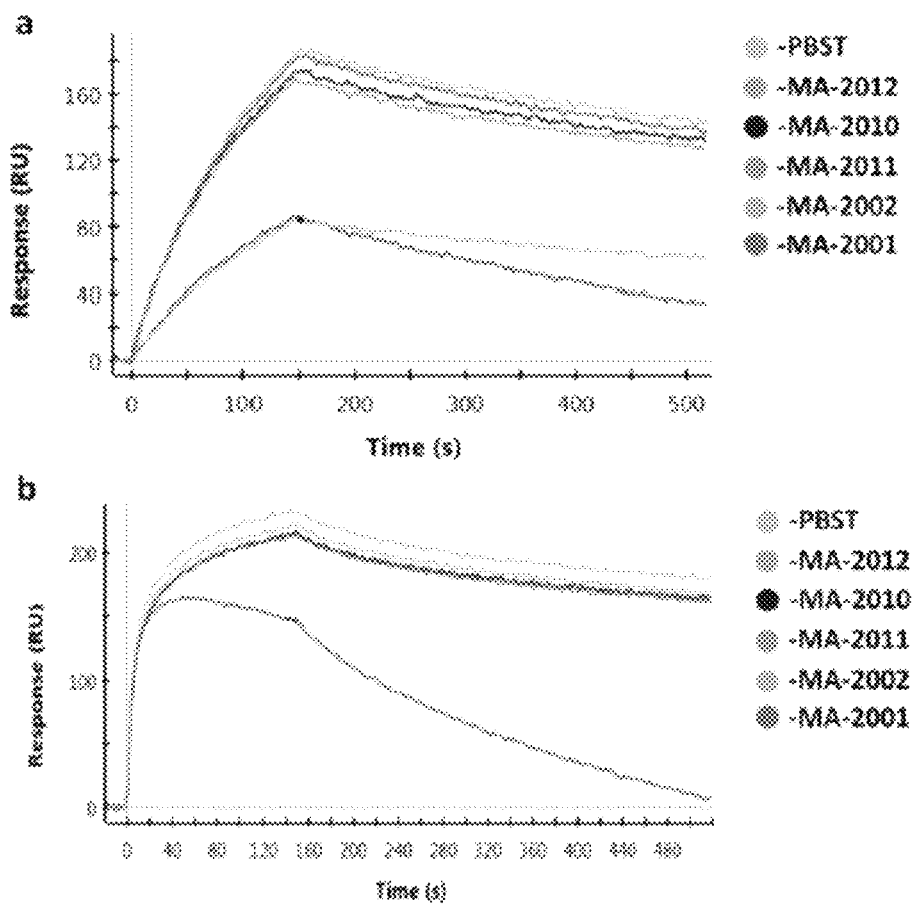

FIG. 12a depicts the binding competition of GyrA-14 with antibodies, in accordance with an embodiment of the present disclosure.

FIG. 12b depicts the binding competition of CcdA 50-72 peptide with antibodies, in accordance with an embodiment of the present disclosure.

Figure 13:
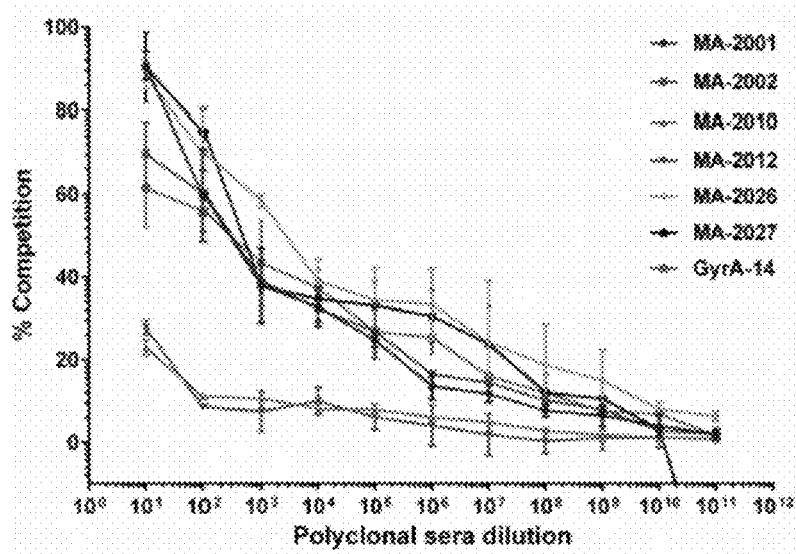

FIG. 13 depicts the competition of mouse mAbs and GyrA-14 with rabbit polyclonal sera, in accordance with an embodiment of the present disclosure.

Figure 14:
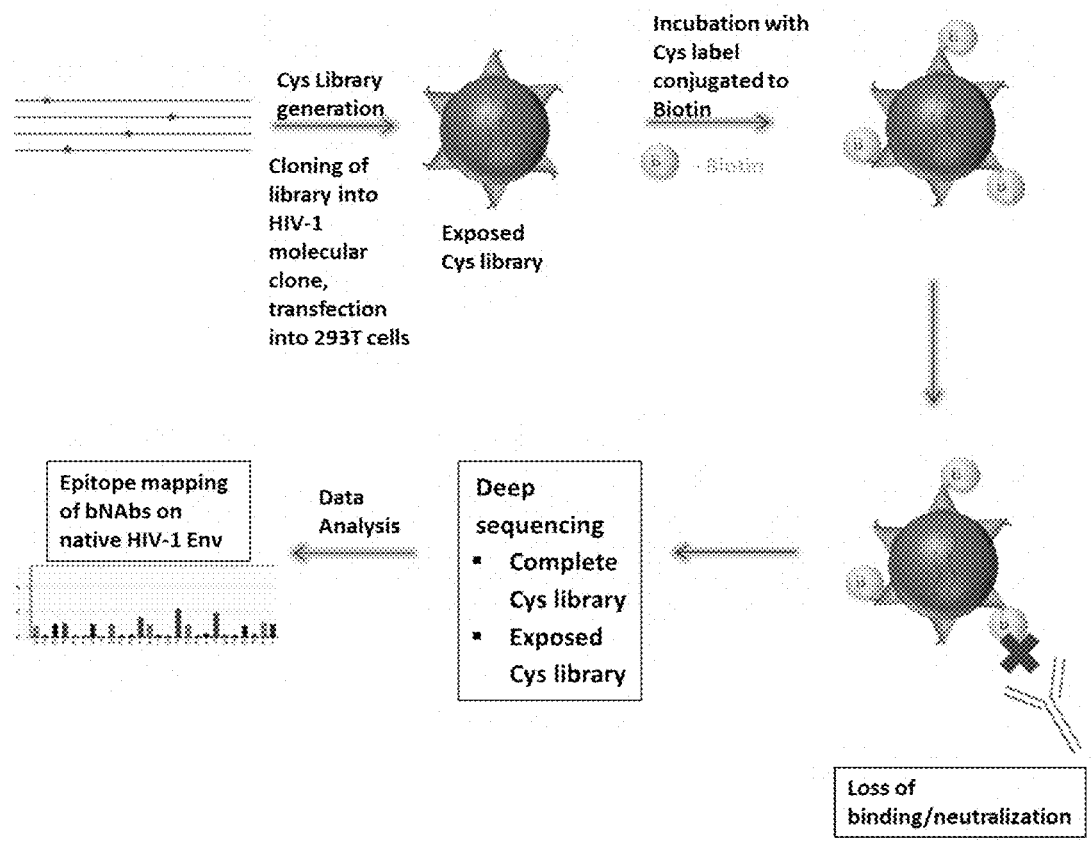

FIG. 14 depicts a schematic of cysteine scanning mutagenesis for epitope mapping of HIV-1 envelope glycoprotein (Env), in accordance with an embodiment of the present disclosure.

Figure 15:
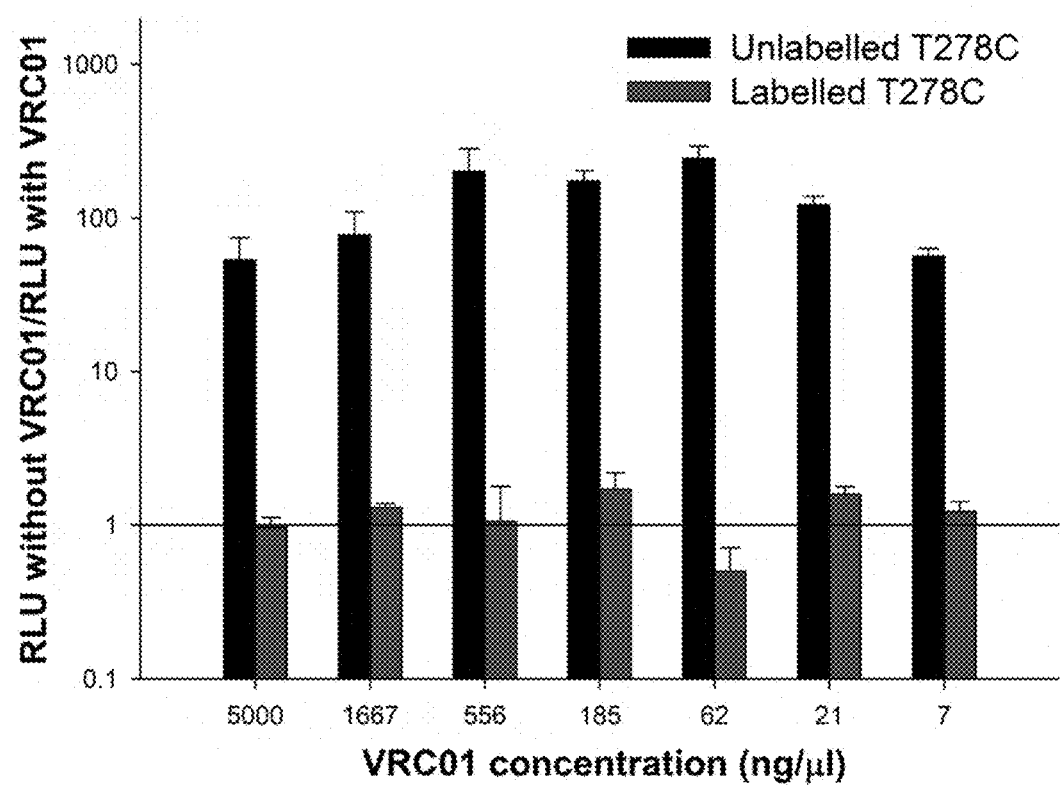

FIG. 15 depicts VRC01 epitope mapping using the T278C mutant virus: The y-axis show the ratio (relative luminescence units without VRC01/relative luminescence units with VRC01) for both the unlabelled and labelled virus, in accordance with an embodiment of the present disclosure.

Figure 16:
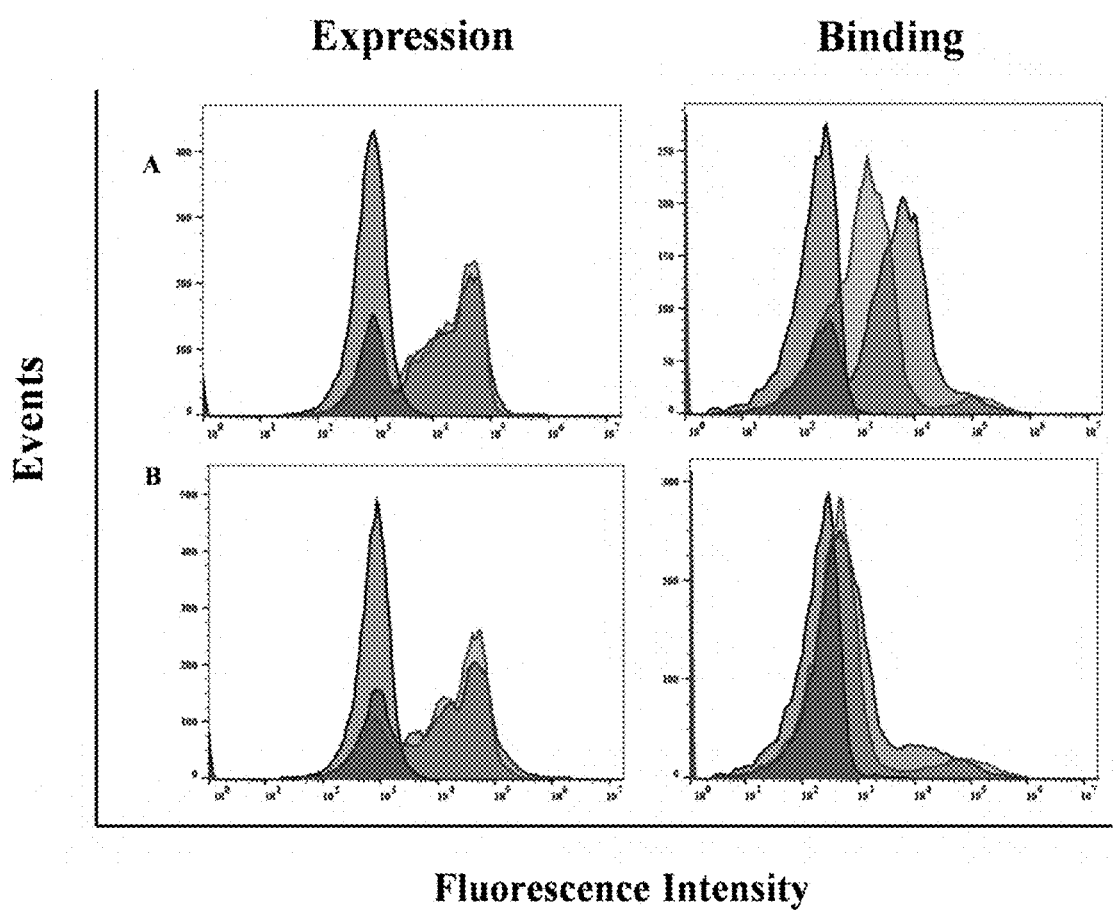

FIG. 16 depicts yeast surface display to monitor the binding and expression of MazE3 (A) and MazF3 (B), in accordance with an embodiment of the present disclosure.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Epitope mapping refers to identification of binding sites (epitopes) of a desired molecule on a protein or antigen of interest. The desired molecule can be DNA, RNA, chemical molecule, biological molecule, peptide, polypeptide, and combinations thereof. The protein or antigen of interest can be a receptor protein or any other protein or antigen that needs to be investigated. Mapping the epitope of an antibody on its corresponding antigen is fundamental to delineate of the mechanisms of molecular recognition and provides the basis for rational vaccine and drug design.

Display population refers to a population that displays on its surface a mutant variant of the protein or antigen for which epitope mapping is to be performed. The display population can be mammalian cells, phage population, viral population, lentiviral population, and yeast cells. For the purposes of this document, members of all the population mentioned previously are referred to as cells.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

Recent advances in mutagenesis methodologies coupled with rapid advances in deep sequencing technology have made such approaches feasible. The cysteine (Cys) labelling methodology has previously been applied to study protein folding and unfolding with individual point mutants containing single Cys residues. These studies require purified proteins. The present disclosure attempts to significantly extend the scope of this methodology by using it for mixtures of mutants, the absence of any protein purification and coupling Cys accessibility assays to genotypic information. The present disclosure also depicts in detail a working example of using the disclosed method of epitope mapping on CcdB antigen, HIV-1 envelope glycoprotein, and TA systems of *Mycobacterium tuberculosis*. In addition to its utility to study HIV-1 Env structure and function, this novel methodology can be easily extended to other viral systems where genotype and phenotype (infectivity or ligand binding) are easily coupled.

The present disclosure is not to be limited in scope by the specific embodiments described herein, which are intended for the purposes of exemplification only. Functionally-equivalent products, compositions, and methods are clearly within the scope of the disclosure, as described herein.

In an embodiment of the present disclosure, there is provided a method of identifying binding sites of a molecule of interest to a receptor protein, said method comprising: (a) obtaining a display population, wherein said population comprises cells, phage or virus (hereafter collectively referred to for convenience as 'cells'), each member expressing on its surface a mutant variant of the receptor protein, wherein said mutant variant has at least a single amino acid residue mutated to an amino acid residue selected from the group consisting of cysteine; (b) contacting a cysteine specific probe with said population, wherein said cysteine specific probe binds to the cysteine residue on the mutant variant; (c) contacting said molecule of interest with said population; and (d) detecting binding of molecule of interest to said mutant variant of the receptor protein, wherein lack of binding of the molecule of interest to the mutant variant is indicative that the corresponding amino acid residue in the receptor protein at the same position as that of the substituted cysteine in the mutated variant is involved in binding of the molecule of interest.

In an embodiment of the present disclosure, there is provided a method of identifying binding sites of a molecule of interest to a receptor protein, said method comprising: (a) obtaining a display population, wherein said population comprises cells, phage or virus (hereafter collectively referred to for convenience as 'cells'), each member expressing on its surface a mutant variant of the receptor protein, wherein said mutant variant has at least a single amino acid residue mutated to an amino acid residue selected from the group consisting of cysteine, alanine, serine, and any other amino acid; (b) contacting a cysteine specific probe with said population, wherein said cysteine specific probe binds to the cysteine residue on the mutant variant; (c) contacting said molecule of interest with said population; and (d) detecting binding of molecule of interest to said mutant variant of the receptor protein, wherein lack of binding of the molecule of interest to the mutant variant is indicative that the corresponding amino acid residue in the receptor protein at the same position as that of the substituted cysteine in the mutated variant is involved in binding of the molecule of interest.

In an embodiment of the present disclosure, there is provided a method of identifying binding sites of a molecule of interest to a receptor protein as described herein, wherein said receptor protein has no cysteine residues, and said mutant variant has a single mutation, wherein said mutation is a substituted cysteine.

In an embodiment of the present disclosure, there is provided a method of identifying binding sites of a molecule of interest to a receptor protein as described herein, wherein said receptor protein has "n" number of cysteine residues involved in binding of molecule of interest, and in said mutant variant, the "n" number of cysteine residues of the receptor protein are substituted with alanine, serine or any other amino acid and further, an additional single substitution to cysteine is made at an amino acid position which is not any of the "n" number of cysteine residues in the receptor protein.

In an embodiment of the present disclosure, there is provided a method of identifying binding sites of a molecule of interest to a receptor protein as described herein, wherein said receptor protein has "n" number of cysteine residues involved in binding of molecule of interest, and in said mutant variant, the "n" number of cysteine residues of the receptor protein are substituted with alanine, and further, an additional single substitution to cysteine is made at an amino acid position which is not any of the "n" number of cysteine residues in the receptor protein.

In an embodiment of the present disclosure, there is provided a method of identifying binding sites of a molecule of interest to a receptor protein as described herein, wherein said receptor protein has "n" number of cysteine residues involved in binding of molecule of interest, and in said mutant variant, the "n" number of cysteine residues of the receptor protein are substituted with serine, and further, an additional single substitution to cysteine is made at an amino acid position which is not any of the "n" number of cysteine residues in the receptor protein.

In an embodiment of the present disclosure, there is provided a method of identifying binding sites of a molecule of interest to a receptor protein as described herein, wherein "n" can be 1.

In an embodiment of the present disclosure, there is provided a method of identifying binding sites of a molecule of interest to a receptor protein as described herein, wherein "n" can be greater than 1.

In an embodiment of the present disclosure, there is provided a method of identifying binding sites of a molecule of interest to a receptor protein as described herein, wherein in said population, each cell expresses the same mutant variant of the receptor protein.

In an embodiment of the present disclosure, there is provided a method of identifying binding sites of a molecule of interest to a receptor protein as described herein, wherein said population comprises two sub-populations, wherein each sub-population comprises cells/members expressing a unique mutant variant.

In an embodiment of the present disclosure, there is provided a method of identifying binding sites of a molecule of interest to a receptor protein as described herein, wherein said population comprises two sub-populations, wherein each sub-population comprises yeast cells expressing a unique mutant variant.

In an embodiment of the present disclosure, there is provided a method of identifying binding sites of a molecule of interest to a receptor protein as described herein, wherein said population comprises more than two sub-populations, wherein each sub-population comprises cells/members expressing a unique mutant variant.

In an embodiment of the present disclosure, there is provided a method of identifying binding sites of a molecule of interest to a receptor protein as described herein, wherein said population comprises more than two sub-populations, wherein each sub-population comprises yeast cells expressing a unique mutant variant.

In an embodiment of the present disclosure, there is provided a method of identifying binding sites of a molecule of interest to a receptor protein as described herein, wherein said mutant variant is tethered to the cell surface.

In an embodiment of the present disclosure, there is provided a method of identifying binding sites of a molecule of interest to a receptor protein as described herein, wherein said population comprises more than 2 sub-populations, wherein each sub-population comprises yeast cells expressing a unique mutant variant, and wherein said mutant variant is tethered to the cell surface.

In an embodiment of the present disclosure, there is provided a method of identifying binding sites of a molecule of interest to a receptor protein as described herein, wherein said cysteine specific probe is selected from the group consisting of, but not limited to Biotin-maleimide, Biotin-PEG2-maleimide, Biotin-PEG11-maleimide, Iodoacetic acid, Methyl methanethiosulfonate, Iodoacetamide, N-Methoxycarbonylmaleimide, Methoxy PEG Maleimide, Ellmans reagent (DTNB), TAMRA maleimide, N-(5-Fluoresceinyl)maleimide, Alexa-maleimides, Tetramethylrhodamine-maleimide, Cyanine maleimide, N-(1-Pyrenyl)maleimide, and Sulfo-Cyanine maleimide, and methane thiosulfonate derivatives In an embodiment of the present disclosure, there is provided a method of identifying binding sites of a molecule of interest to a receptor protein as described herein, wherein said cysteine specific probe is biotin-PEG2-maleimide.

In an embodiment of the present disclosure, there is provided a method of identifying binding sites of a molecule of interest to a receptor protein as described herein, wherein said cysteine specific probe binds specifically to cysteine residues.

In an embodiment of the present disclosure, there is provided a method of identifying binding sites of a molecule of interest to a receptor protein as described herein, wherein said cysteine specific probe binds only to surface exposed cysteine residues.

In an embodiment of the present disclosure, there is provided a method of identifying binding sites of a molecule of interest to a receptor protein as described herein, wherein said cysteine specific probe binds to buried cysteine residues in the presence of at least one denaturant.

In an embodiment of the present disclosure, there is provided a method of identifying binding sites of a molecule of interest to a receptor protein as described herein, wherein said molecule of interest is selected from the group consisting of antibody or fragments thereof, DNA, RNA, chemical molecule, biological molecule, peptide, polypeptide, and combinations thereof.

In an embodiment of the present disclosure, there is provided a method of identifying binding sites of a molecule of interest to a receptor protein as described herein, wherein said molecule of interest is an antibody.

In an embodiment of the present disclosure, there is provided a method of identifying binding sites of a molecule of interest to a receptor protein as described herein, wherein said display population is selected from the group consisting of yeast display library, phage display library, viral display library, lentiviral display library, and mammalian surface display library.

In an embodiment of the present disclosure, there is provided a method of identifying binding sites of a molecule of interest to a receptor protein as described herein, wherein said display population is a yeast display library.

In an embodiment of the present disclosure, there is provided a method of identifying binding sites of a molecule of interest to a receptor protein as described herein, wherein said display population is a phage display library.

In an embodiment of the present disclosure, there is provided a method of identifying binding sites of a molecule of interest to a receptor protein as described herein, wherein said display library is a viral or lentiviral display library.

In an embodiment of the present disclosure, there is provided a method of identifying binding sites of a molecule of interest to a receptor protein as described herein, wherein said display population is a mammalian surface display library.

In an embodiment of the present disclosure, there is provided a method of identifying binding sites of a molecule of interest to a receptor protein as described herein, wherein said yeast, phage, or lentiviral display population is prepared by: (a) obtaining a receptor protein; (b) creating a population of receptor protein mutant variants, wherein each mutant variant contains a single amino acid residue mutated to a cysteine; and (c) tethering mutant variants to yeast cell, mammalian cell, phage or virus to obtain a surface display population.

In an embodiment of the present disclosure, there is provided a method of identifying binding sites of a molecule of interest to a receptor protein as described herein, wherein said display population is a yeast display population, and wherein the yeast display population is prepared by: (a) obtaining a receptor protein; (b) creating a population of receptor protein mutant variants, wherein each mutant variant contains a single amino acid residue mutated to a cysteine; and (c) tethering mutant variants to yeast cell to obtain a yeast surface display population.

In an embodiment of the present disclosure, there is provided a method of identifying binding sites of a molecule of interest to a receptor protein as described herein, wherein said display population is a phage display population, and wherein the phage display population is prepared by: (a) obtaining a receptor protein; (b) creating a population of receptor protein mutant variants, wherein each mutant variant contains a single amino acid residue mutated to a cysteine; and (c) tethering mutant variants to phage surface to obtain a phage surface display population.

In an embodiment of the present disclosure, there is provided a method of identifying binding sites of a molecule of interest to a receptor protein as described herein, wherein said display population is a lentiviral display population, and wherein the lentiviral display population is prepared by: (a) obtaining a receptor protein; (b) creating a population of receptor protein mutant variants, wherein each mutant variant contains a single amino acid residue mutated to a cysteine; and (c) tethering mutant variants to lentiviral surface to obtain a lentiviral surface display population.

In an embodiment of the present disclosure, there is provided a method of identifying binding sites of a molecule of interest to a receptor protein as described herein, wherein said display population is a mammalian surface display population, and wherein the lentiviral display population is prepared by: (a) obtaining a receptor protein; (b) creating a population of receptor protein mutant variants, wherein each mutant variant contains a single amino acid residue mutated to a cysteine; and (c) tethering mutant variants to mammalian surface to obtain a mammalian surface display population.

In an embodiment of the present disclosure, there is provided a yeast surface display library, wherein each member of the library has tethered to its surface a receptor protein mutant variant, wherein each variant has at least a single amino acid residue mutated to cysteine.

In an embodiment of the present disclosure, there is provided a yeast surface display library, wherein each member of the library has tethered to its surface a receptor protein mutant variant, wherein each variant has at least a single amino acid residue mutated to an amino acid residue selected from the group consisting of cysteine, serine, alanine, and any other amino acid.

In an embodiment of the present disclosure, there is provided a yeast surface display library as described herein, wherein said receptor protein has no cysteine residues, each variant has a single mutation, and said mutation is a substituted cysteine.

In an embodiment of the present disclosure, there is provided a yeast surface display library as described herein, wherein said receptor protein has no cysteine residues, each variant has a single mutation, and said mutation is a substituted serine.

In an embodiment of the present disclosure, there is provided a yeast surface display library as described herein, wherein said receptor protein has no cysteine residues, each variant has a single mutation, and said mutation is a substituted alanine.

In an embodiment of the present disclosure, there is provided a yeast surface display library as described herein, wherein said receptor protein has "n" number of cysteine residues involved in binding of molecule of interest, and in each mutant variant, the "n" number of cysteine residues of the receptor protein are substituted with alanine, serine or any other amino acid, and further, an additional single substitution to cysteine is made at an amino acid position which is not any of the "n" number of cysteine residues in the receptor protein.

In an embodiment of the present disclosure, there is provided a yeast surface display library as described herein, wherein said receptor protein has "n" number of cysteine residues involved in binding of molecule of interest, and in each mutant variant, the "n" number of cysteine residues of the receptor protein are substituted with alanine, and further, an additional single substitution to cysteine is made at an amino acid position which is not any of the "n" number of cysteine residues in the receptor protein.

In an embodiment of the present disclosure, there is provided a yeast surface display library as described herein, wherein said receptor protein has "n" number of cysteine residues involved in binding of molecule of interest, and in each mutant variant, the "n" number of cysteine residues of the receptor protein are substituted with serine, and further, an additional single substitution to cysteine is made at an amino acid position which is not any of the "n" number of cysteine residues in the receptor protein.

In an embodiment of the present disclosure, there is provided a yeast surface display library as described herein, wherein "n" is 1.

In an embodiment of the present disclosure, there is provided a yeast surface display library as described herein, wherein "n" is greater than 1.

In an embodiment of the present disclosure, there is provided a yeast surface display library as described herein, wherein said library comprises a population of cells with a single type of mutant variant tethered to the cell surface.

In an embodiment of the present disclosure, there is provided a yeast surface display library as described herein, wherein said library comprises at least two sub-populations, wherein each subpopulation comprises cells with a single type of mutant variant tethered to the cell surface.

In an embodiment of the present disclosure, there is provided a phage surface display library, wherein each member of the library has tethered to its surface a receptor protein mutant variant, wherein each variant has at least a single amino acid residue mutated to an amino acid residue that is cysteine or an amino acid selected from the group consisting of cysteine, serine, and alanine.

In an embodiment of the present disclosure, there is provided a phage surface display library as described herein, wherein said receptor protein has no cysteine residues, each variant has a single mutation, and said mutation is a substituted cysteine.

In an embodiment of the present disclosure, there is provided a phage surface display library as described herein, wherein said receptor protein has "n" number of cysteine residues involved in binding of molecule of interest, and in each mutant variant, the "n" number of cysteine residues of the receptor protein are substituted with alanine, serine or any other amino acid residue, and further, an additional single substitution to cysteine is made at an amino acid position which is not any of the "n" number of cysteine residues in the receptor protein.

In an embodiment of the present disclosure, there is provided a phage surface display library as described herein, wherein said receptor protein has "n" number of cysteine residues involved in binding of molecule of interest, and in each mutant variant, the "n" number of cysteine residues of the receptor protein are substituted with alanine, and further, an additional single substitution to cysteine is made at an amino acid position which is not any of the "n" number of cysteine residues in the receptor protein.

In an embodiment of the present disclosure, there is provided a phage surface display library as described herein, wherein said receptor protein has "n" number of cysteine residues involved in binding of molecule of interest, and in each mutant variant, the "n" number of cysteine residues of the receptor protein are substituted with serine, and further, an additional single substitution to cysteine is made at an amino acid position which is not any of the "n" number of cysteine residues in the receptor protein.

In an embodiment of the present disclosure, there is provided a phage surface display library as described herein, wherein "n" is 1.

In an embodiment of the present disclosure, there is provided a phage surface display library as described herein, wherein "n" is greater than 1.

In an embodiment of the present disclosure, there is provided a phage surface display library as described herein, wherein said comprises a population of cells with a single type of mutant variant tethered to the cell surface.

In an embodiment of the present disclosure, there is provided a phage surface display library as described herein, wherein said library comprises at least two sub-populations, wherein each subpopulation comprises cells with a single type of mutant variant tethered to the cell surface.

In an embodiment of the present disclosure, there is provided a lentiviral display library or a mammalian surface display library, wherein each member of the library has tethered to its surface a receptor protein mutant variant, wherein each variant has at least a single amino acid residue mutated to an amino acid residue is cysteine or an amino acid selected from the group consisting of cysteine, serine, alanine and any other amino acid.

In an embodiment of the present disclosure, there is provided a lentiviral display library or a mammalian surface display library as described herein, wherein said receptor protein has no cysteine residues, each variant has a single mutation, and said mutation is a substituted cysteine.

In an embodiment of the present disclosure, there is provided a yeast surface display library as described herein, wherein said receptor protein has "n" number of cysteine residues involved in binding of molecule of interest, and in each mutant variant, the "n" number of cysteine residues of the receptor protein are substituted with alanine, serine or any other amino acid, and further, an additional single substitution to cysteine is made at an amino acid position which is not any of the "n" number of cysteine residues in the receptor protein.

In an embodiment of the present disclosure, there is provided a lentiviral display library or a mammalian surface display library as described herein, wherein said receptor protein has "n" number of cysteine residues involved in binding of molecule of interest, and in each mutant variant, the "n" number of cysteine residues of the receptor protein are substituted with alanine, and further, an additional single substitution to cysteine is made at an amino acid position which is not any of the "n" number of cysteine residues in the receptor protein.

In an embodiment of the present disclosure, there is provided a lentiviral display library or a mammalian surface display library as described herein, wherein said receptor protein has "n" number of cysteine residues involved in binding of molecule of interest, and in each mutant variant, the "n" number of cysteine residues of the receptor protein are substituted with serine, and further, an additional single substitution to cysteine is made at an amino acid position which is not any of the "n" number of cysteine residues in the receptor protein.

In an embodiment of the present disclosure, there is provided a lentiviral display library or a mammalian surface display library as described herein, wherein "n" is 1.

In an embodiment of the present disclosure, there is provided a lentiviral display library or a mammalian surface display library as described herein, wherein "n" is greater than 1.

In an embodiment of the present disclosure, there is provided a lentiviral display library or a mammalian surface display library as described herein, wherein said comprises a population of cells with a single type of mutant variant tethered to the cell surface.

In an embodiment of the present disclosure, there is provided a lentiviral display library or a mammalian surface display library as described herein, wherein said library comprises at least two sub-populations, wherein each sub-population comprises cells with a single type of mutant variant tethered to the cell surface.

In an embodiment of the present disclosure, there is provided a method of preparing a yeast surface display library, wherein each member of the library has tethered to its surface a receptor protein mutant variant, wherein said receptor protein has no cysteine residues, and each variant has a single amino acid residue mutated to cysteine; said method comprising: (a) obtaining a receptor protein; (b) creating a population of receptor protein mutant variants, wherein each mutant variant contains a single amino acid residue mutated to cysteine; and (c) tethering mutant variants to yeast cells to obtain a yeast surface display library.

In an embodiment of the present disclosure, there is provided a method of preparing a phage surface display library, wherein each member of the library has tethered to its surface a receptor protein mutant variant, wherein said receptor protein has no cysteine residues, and each variant has a single amino acid residue mutated to cysteine; said method comprising: (a) obtaining a receptor protein; (b) creating a population of receptor protein mutant variants, wherein each mutant variant contains a single amino acid residue mutated to cysteine; and (c) tethering mutant variants to phage to obtain a phage surface display library.

In an embodiment of the present disclosure, there is provided a method of preparing a viral surface display or mammalian cell surface display library, wherein each member of the library has tethered to its surface a receptor protein mutant variant, wherein said receptor protein has no cysteine residues, and each variant has a single amino acid residue mutated to cysteine; said method comprising: (a) obtaining a receptor protein; (b) creating a population of receptor protein mutant variants, wherein each mutant variant contains a single amino acid residue mutated to cysteine; and (c) tethering mutant variants to display library or a mammalian surface display library cells transfected with the lentiviral library so as to obtain a lentiviral surface display library.

In an embodiment of the present disclosure, there is provided a method of preparing a yeast surface display library, wherein each member of the library has tethered to its surface a receptor protein mutant variant, wherein said receptor protein has "n" number of cysteine residues involved in binding of molecule of interest, where n=1; said method comprising: (a) obtaining a receptor protein, wherein said receptor protein has "n" number of cysteine residues involved in binding of molecule of interest; (b) creating a population of receptor protein mutant variants, wherein in each mutant variant, the "n" number of cysteine residues of the receptor protein are substituted with alanine, and further, an additional single substitution to cysteine is made at an amino acid position which is not any of the "n" number of cysteine residues in the receptor protein; and (c) tethering mutant variants to yeast cells to obtain a surface display library.

In an embodiment of the present disclosure, there is provided a method of preparing a yeast surface display library, wherein each member of the library has tethered to its surface a receptor protein mutant variant, wherein said receptor protein has "n" number of cysteine residues involved in binding of molecule of interest, where n=1; said method comprising: (a) obtaining a receptor protein, wherein said receptor protein has "n" number of cysteine residues involved in binding of molecule of interest; (b) creating a population of receptor protein mutant variants, wherein in each mutant variant, the "n" number of cysteine residues of the receptor protein are substituted with serine, and further, an additional single substitution to cysteine is made at an amino acid position which is not any of the "n" number of cysteine residues in the receptor protein; and (c) tethering mutant variants to yeast cells to obtain a surface display library.

In an embodiment of the present disclosure, there is provided a method of preparing a yeast surface display library, wherein each member of the library has tethered to its surface a receptor protein mutant variant, wherein said receptor protein has "n" number of cysteine residues involved in binding of molecule of interest, where n>1; said method comprising: (a) obtaining a receptor protein, wherein said receptor protein has "n" number of cysteine residues involved in binding of molecule of interest; (b) creating a population of receptor protein mutant variants, wherein in each mutant variant, the "n" number of cysteine residues of the receptor protein are substituted with alanine, and further, an additional single substitution to cysteine is made at an amino acid position which is not any of the "n" number of cysteine residues in the receptor protein; and (c) tethering mutant variants to yeast cells to obtain a surface display library.

In an embodiment of the present disclosure, there is provided a method of preparing a yeast surface display library, wherein each member of the library has tethered to its surface a receptor protein mutant variant, wherein said receptor protein has "n" number of cysteine residues involved in binding of molecule of interest, where n>1; said method comprising: (a) obtaining a receptor protein, wherein said receptor protein has "n" number of cysteine residues involved in binding of molecule of interest; (b) creating a population of receptor protein mutant variants, wherein in each mutant variant, the "n" number of cysteine residues of the receptor protein are substituted with serine, and further, an additional single substitution to cysteine is made at an amino acid position which is not any of the "n" number of cysteine residues in the receptor protein; and (c) tethering mutant variants to yeast cells to obtain a surface display library.

In an embodiment of the present disclosure, there is provided a method of preparing a phage surface display library, wherein each member of the library has tethered to its surface a receptor protein mutant variant, wherein said receptor protein has "n" number of cysteine residues involved in binding of molecule of interest, where n=1; said method comprising: (a) obtaining a receptor protein, wherein said receptor protein has "n" number of cysteine residues involved in binding of molecule of interest; (b) creating a population of receptor protein mutant variants, wherein in each mutant variant, the "n" number of cysteine residues of the receptor protein are substituted with alanine, and further, an additional single substitution to cysteine is made at an amino acid position which is not any of the "n" number of cysteine residues in the receptor protein; and (c) tethering mutant variants to the surface of phage to obtain a phage surface display library.

In an embodiment of the present disclosure, there is provided a method of preparing a phage surface display library, wherein each member of the library has tethered to its surface a receptor protein mutant variant, wherein said receptor protein has "n" number of cysteine residues involved in binding of molecule of interest, where n=1; said method comprising: (a) obtaining a receptor protein, wherein said receptor protein has "n" number of cysteine residues involved in binding of molecule of interest; (b) creating a population of receptor protein mutant variants, wherein in each mutant variant, the "n" number of cysteine residues of the receptor protein are substituted with serine, and further, an additional single substitution to cysteine is made at an amino acid position which is not any of the "n" number of cysteine residues in the receptor protein; and (c) tethering mutant variants to phage to obtain a surface display library.

In an embodiment of the present disclosure, there is provided a method of preparing a phage surface display library, wherein each member of the library has tethered to its surface a receptor protein mutant variant, wherein said receptor protein has "n" number of cysteine residues involved in binding of molecule of interest, where n>1; said method comprising: (a) obtaining a receptor protein, wherein said receptor protein has "n" number of cysteine residues involved in binding of molecule of interest; (b) creating a population of receptor protein mutant variants, wherein in each mutant variant, the "n" number of cysteine residues of the receptor protein are substituted with alanine, and further, an additional single substitution to cysteine is made at an amino acid position which is not any of the "n" number of cysteine residues in the receptor protein; and (c) tethering mutant variants to phage to obtain a surface display library.

In an embodiment of the present disclosure, there is provided a method of preparing a phage surface display library, wherein each member of the library has tethered to its surface a receptor protein mutant variant, wherein said receptor protein has "n" number of cysteine residues involved in binding of molecule of interest, where n>1; said method comprising: (a) obtaining a receptor protein, wherein said receptor protein has "n" number of cysteine residues involved in binding of molecule of interest; (b) creating a population of receptor protein mutant variants, wherein in each mutant variant, the "n" number of cysteine residues of the receptor protein are substituted with serine, and further, an additional single substitution to cysteine is made at an amino acid position which is not any of the "n" number of cysteine residues in the receptor protein; and (c) tethering mutant variants to phage to obtain a surface display library.

In an embodiment of the present disclosure, there is provided a method of preparing a lentiviral display library or a mammalian surface display library, wherein each member of the library has tethered to its surface a receptor protein mutant variant, wherein said receptor protein has "n" number of cysteine residues involved in binding of molecule of interest, where n=1; said method comprising: (a) obtaining a receptor protein, wherein said receptor protein has "n" number of cysteine residues involved in binding of molecule of interest; (b) creating a population of receptor protein mutant variants, wherein in each mutant variant, the "n" number of cysteine residues of the receptor protein are substituted with alanine, and further, an additional single substitution to cysteine is made at an amino acid position which is not any of the "n" number of cysteine residues in the receptor protein; and (c) tethering mutant variants to cells transfected with lentivirus to obtain a surface display library.

In an embodiment of the present disclosure, there is provided a method of preparing a lentiviral display library or a mammalian surface display library, wherein each member of the library has tethered to its surface a receptor protein mutant variant, wherein said receptor protein has "n" number of cysteine residues involved in binding of molecule of interest, where n=1; said method comprising: (a) obtaining a receptor protein, wherein said receptor protein has "n" number of cysteine residues involved in binding of molecule of interest; (b) creating a population of receptor protein mutant variants, wherein in each mutant variant, the "n" number of cysteine residues of the receptor protein are substituted with serine, and further, an additional single substitution to cysteine is made at an amino acid position which is not any of the "n" number of cysteine residues in the receptor protein; and (c) tethering mutant variants to cells transfected with lentivirus to obtain a surface display library.

In an embodiment of the present disclosure, there is provided a method of preparing a lentiviral display library or a mammalian surface display library, wherein each member of the library has tethered to its surface a receptor protein mutant variant, wherein said receptor protein has "n" number of cysteine residues involved in binding of molecule of interest, where n>1; said method comprising: (a) obtaining a receptor protein, wherein said receptor protein has "n" number of cysteine residues involved in binding of molecule of interest; (b) creating a population of receptor protein mutant variants, wherein in each mutant variant, the "n" number of cysteine residues of the receptor protein are substituted with alanine, and further, an additional single substitution to cysteine is made at an amino acid position which is not any of the "n" number of cysteine residues in the receptor protein; and (c) tethering mutant variants to cells infected with lentivirus to obtain a surface display library.

In an embodiment of the present disclosure, there is provided a method of preparing a lentiviral display library or a mammalian surface display library, wherein each member of the library has tethered to its surface a receptor protein mutant variant, wherein said receptor protein has "n" number of cysteine residues involved in binding of molecule of interest, where n>1; said method comprising: (a) obtaining a receptor protein, wherein said receptor protein has "n" number of cysteine residues involved in binding of molecule of interest; (b) creating a population of receptor protein mutant variants, wherein in each mutant variant, the "n" number of cysteine residues of the receptor protein are substituted with serine, and further, an additional single substitution to cysteine is made at an amino acid position which is not any of the "n" number of cysteine residues in the receptor protein; and (c) tethering mutant variants to cells infected with lentivirus to obtain a surface display library.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

Figure 1:
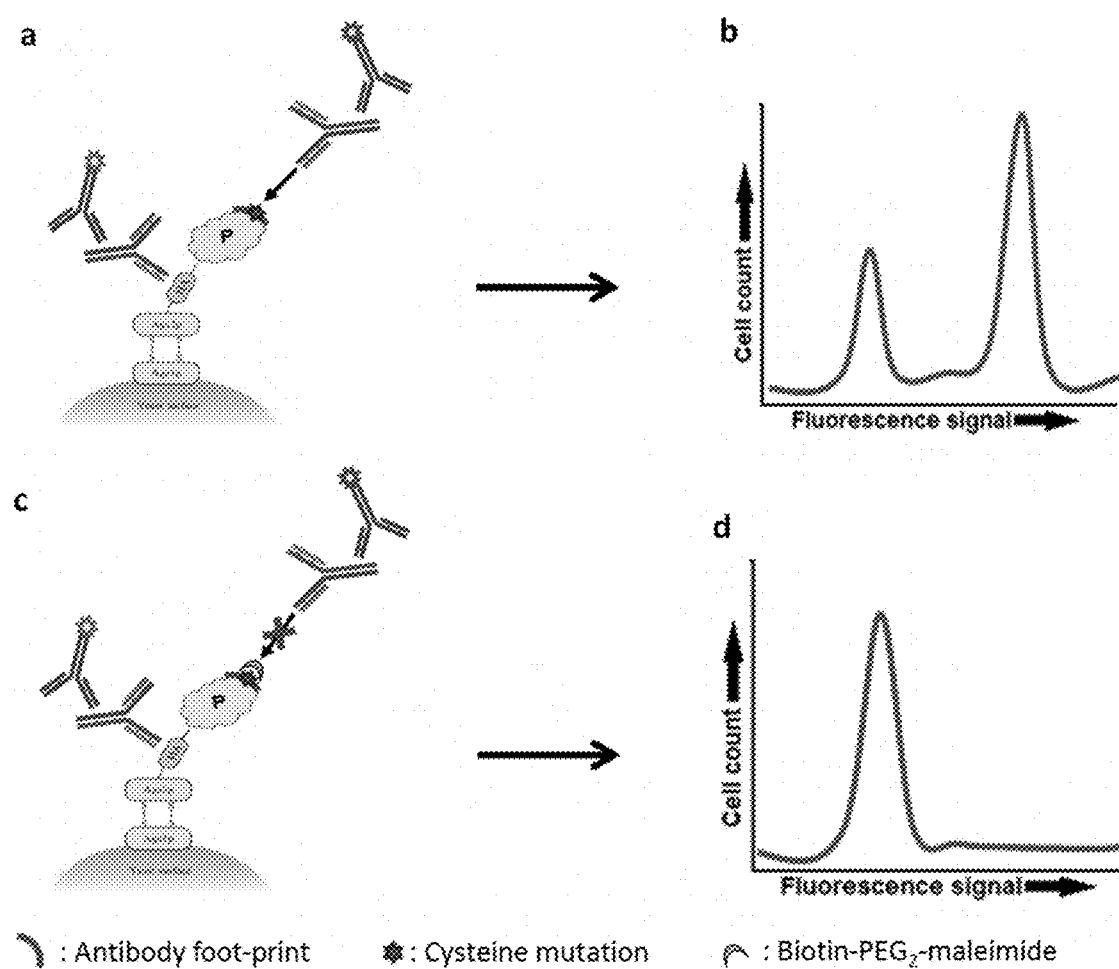
FIG. 1 depicts the schematic outline of the epitope mapping method of identifying the binding sites of a molecule of interest to a receptor protein, in accordance with an embodiment of the present disclosure.

Principle of the Method:

A schematic outline of the method is given in FIG. 1. Briefly, a panel of single cysteine mutants covering the entire surface of the CcdB antigen was made and subsequently cloned these mutants into the yeast surface display vector pPNLS. The plasmids containing the cysteine mutants were individually transformed into the yeast strain EBY100. Cells expressing the mutant protein, tethered to the yeast surface, were surface labeled by biotin-PEG2-maleimide. This probe reacts with all cysteine residues on the yeast surface, including on the CcdB protein. Subsequently, a panel of MAbs was screened by FACS for the loss of binding to the displayed labeled mutant proteins. The CcdB residues which displayed loss of antibody binding, following labeling, form part of the antibody epitope. Additionally, the Examples 8 and 9 display the epitope mapping using the method as described in the present disclosure on HIV-1 antigen and TA (Toxin/Anti-toxin) systems of *Mycobacterium tuberculosis*.

Example 1

Figure 3:
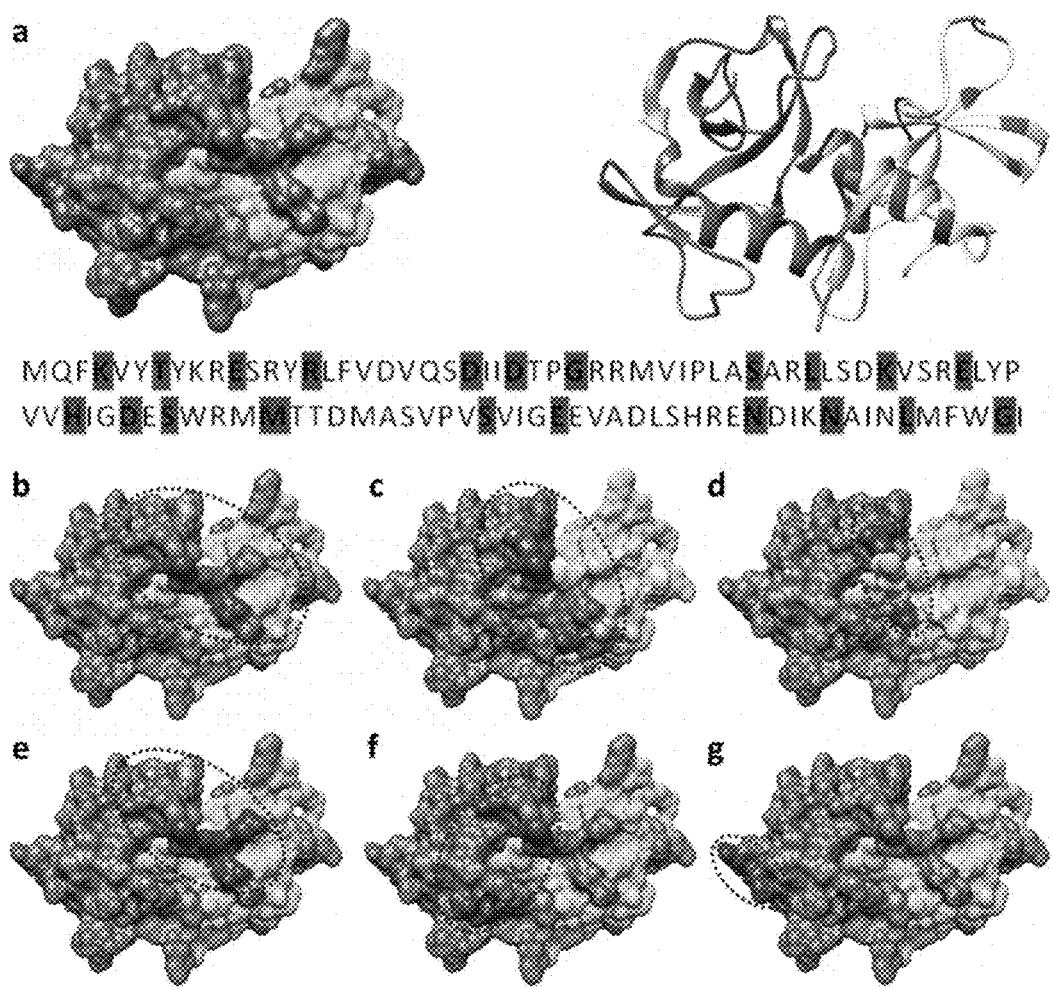
FIG. 3a depicts the surface and ribbon diagram of CcdB protein with residues mutated to cysteine highlighted, in accordance with an embodiment of the present disclosure.
FIG. 3b depicts the residues important for GyrA-14 binding as identified by the method of the instant disclosure, in accordance with an embodiment of the present disclosure.
FIG. 3c depicts the residues important for GyrA-14 binding to CcdB based on crystal structure data, in accordance with an embodiment of the present disclosure.
FIG. 3d depicts the residues important for GyrA-14 binding to CcdB based on saturation mutagenesis data (prior art), in accordance with an embodiment of the present disclosure.
FIG. 3e depicts the residues which form a conformational epitope for MA-2001, in accordance with an embodiment of the present disclosure.
FIG. 3f depicts the residues which form a conformational epitope for MA-2002, in accordance with an embodiment of the present disclosure.
FIG. 3g depicts the residues which form a conformational epitope for MA-2005, 2009, 2010, 2011, 2012, 2014, 2016, 2017, 2018, 2022, and 2023, in accordance with an embodiment of the present disclosure.
Figure 4:
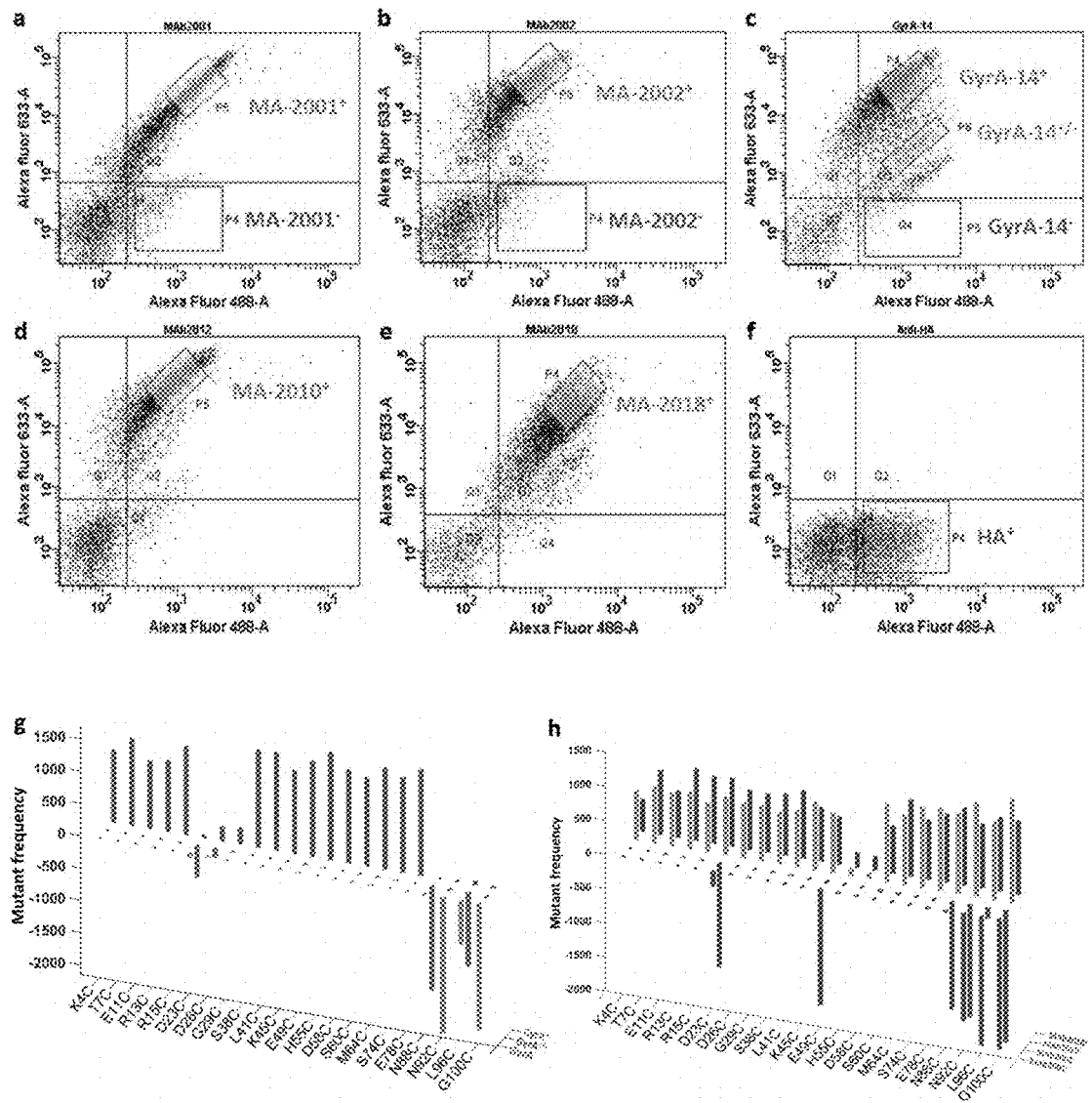
FIG. 4a depicts the FACS sort of labeled mutant pool of CcdB probed with mAb MA-2001 plus anti-HA, in accordance with an embodiment of the present disclosure.
FIG. 4b depicts the FACS sort of labeled mutant pool of CcdB probed with mAb MA-2002 plus anti-HA, in accordance with an embodiment of the present disclosure.
FIG. 4c depicts the FACS sort of labeled mutant pool of CcdB probed with GyrA-14 plus anti-HA, in accordance with an embodiment of the present disclosure.
FIG. 4d depicts the FACS sort of labeled mutant pool of CcdB probed with mAb MA-2010 plus anti-HA, in accordance with an embodiment of the present disclosure.
FIG. 4e depicts the FACS sort of labeled mutant pool of CcdB probed with mAb MA-2018 plus anti-HA, in accordance with an embodiment of the present disclosure.
FIG. 4f depicts the FACS sort of labeled mutant pool of CcdB probed with anti-HA, in accordance with an embodiment of the present disclosure.
FIG. 4g depicts the deep sequencing results plotted as mutant frequency (Y axis) of a particular cysteine mutant (X axis) both bound (+) and not bound (−) to GyrA-14, in accordance with an embodiment of the present disclosure.
FIG. 4h depicts the deep sequencing results plotted as mutant frequency (Y axis) of a particular cysteine mutant (X axis) bound (+) to mAb MA 2010/2018 and not bound (−) to mAb MA 2001/2, in accordance with an embodiment of the present disclosure.

Surface Accessibility Calculations and Design of Single Cysteine Mutants:

To cover the entire surface of CcdB protein, a panel of single cysteine mutants was generated. Twenty-one residues which showed greater than 20% of total side chain accessibility were selected and mutated to cysteine individually (FIG. 3). To make the single cysteine mutant library, first the CcdB WT gene was cloned into the yeast surface display vector pPNLS between two SfiI restriction-sites, so that the cloned gene was in-frame with the endogenous yeast signal peptide, AGA2p and HA tag at the N-terminal end. The c-myc tag fused to the C terminus of CcdB gene in the pPNLS vector was removed by introducing two stop codons to enable the binding of the GyrA-14 protein fragment.

Thirty nucleotide-long overlapping primers were designed to generate the twenty-one cysteine mutants. The primers were synthesized at the PAN Oligo Facility at Stanford University, USA. Vector specific forward primer and reverse mutagenic primer (containing the mutant codon) were used to amplify one overlapping fragment. Similarly, forward mutagenic primer (containing the mutant codon) and the vector specific reverse primer were used to amplify the other overlapping fragment. All the PCR reactions were carried out with Phusion DNA polymerase (Finnzymes). pPNLS vector containing ~1 kb stuffer sequence was digested with SfiI (New England Biolabs) to remove the stuffer insert and gel purified. The digested vector and the two CcdB overlapping fragments were transformed in *S. cerevisiae* EBY100 (Gietz and Schiestl, 2007). Single colonies were picked up, grown to saturation in 3 mL of liquid synthetic SDCAA medium (20 g/L dextrose, 6.7 g/L Difco yeast nitrogen base, 5 g/L Bactocasamino acids, 14.7 g/L sodium citrate, 4.29 g/L citric acid; pH 4.5) and plasmid was extracted by a Phenol:Chloroform:Isoamylalcohol mixture (SRL Laboratories) as described elsewhere (Hoffman and Winston, 1987). The crude plasmid was transformed into *E. coli* DH5α cells to obtain enough plasmid for sequencing. All the mutants were generated individually by this method and were sequence confirmed by Sanger sequencing (Macrogen Inc.). In order to introduce mutations, in other proteins, which possess cysteine residues in predicted binding sites or the protein surface, mutagenesis can be carried out in the manner prescribed above.

Example 2

Yeast Surface Display of Single Cysteine Mutants:

All the sequence confirmed CcdB cysteine mutants cloned into pPNLS vector were individually transformed into the yeast strain EBY100 by LiAc/SS carrier DNA/PEG method (Gietz and Schiestl, 2007). Expression of the displayed proteins on the yeast cell surface was performed (Boder and Wittrup, 1997). Briefly, a single colony was inoculated into 3 ml of liquid synthetic SDCAA medium and grown at 30° C. under shaking conditions (250 rpm) until an $OD_{600}$ of 3-4 was reached. Yeast cells were then induced for protein display by transferring to synthetic SGCAA medium (same as SDCAA medium except containing 20 g/L galactose instead of dextrose) and incubated with shaking at 20° C. for 24 h. After induction, a total of $1 \times 10^6$ yeast cells were washed with PBS containing 0.5% BSA and 1 mM EDTA (PBSB).

To monitor the surface expression of the displayed cysteine mutants, yeast cells were probed with anti-HA chicken antibody (1:250 dilution; Sigma Aldrich Inc.), directed towards the N terminal HA tag, in a final volume of 50 μL, for 1 h at 4° C. The cells were then washed thrice with ice cold PBSB buffer and subsequently stained with Alexa Fluor-488 goat anti-chicken antibody (1:250 dilution; Life Technologies) in a final volume of 50 μL for 30 min at 4° C. in the dark. After washing, the yeast cells were resuspended in 500 μL ice cold PBSB buffer and subjected to flow cytometry (Accuri C6 flow cytometer, BD Biosciences). The data was analyzed using BD CSampler Software (BD Biosciences).

The conformational integrity of displayed cysteine mutant proteins was detected individually by binding to GyrA-14 (a 14 kDa fragment of gyrase A) having a C-terminal 3×FLAG tag. Yeast cells ($1 \times 10^6$ in total from each mutant) were incubated with 50 μL of 100 nM GyrA-14 in PBSB for 1 h at 4° C. GyrA-14 labeled cells were probed with mouse anti-FLAG antibody (1:250 dilution; Sigma Aldrich Inc.) for 1 h at 4° C. After washing thrice with ice cold PBSB buffer, cells were stained with Alexa Fluor-633 goat anti-mouse antibody (1:500 dilutions) for 1 h at 4° C. in dark. The stained yeast cells were resuspended in 500 μL PBSB and subjected to flow cytometry (Accuri C6 flow cytometer, BD Biosciences). The data was analyzed using BD CSampler Software (BD Biosciences).

Figure 2:
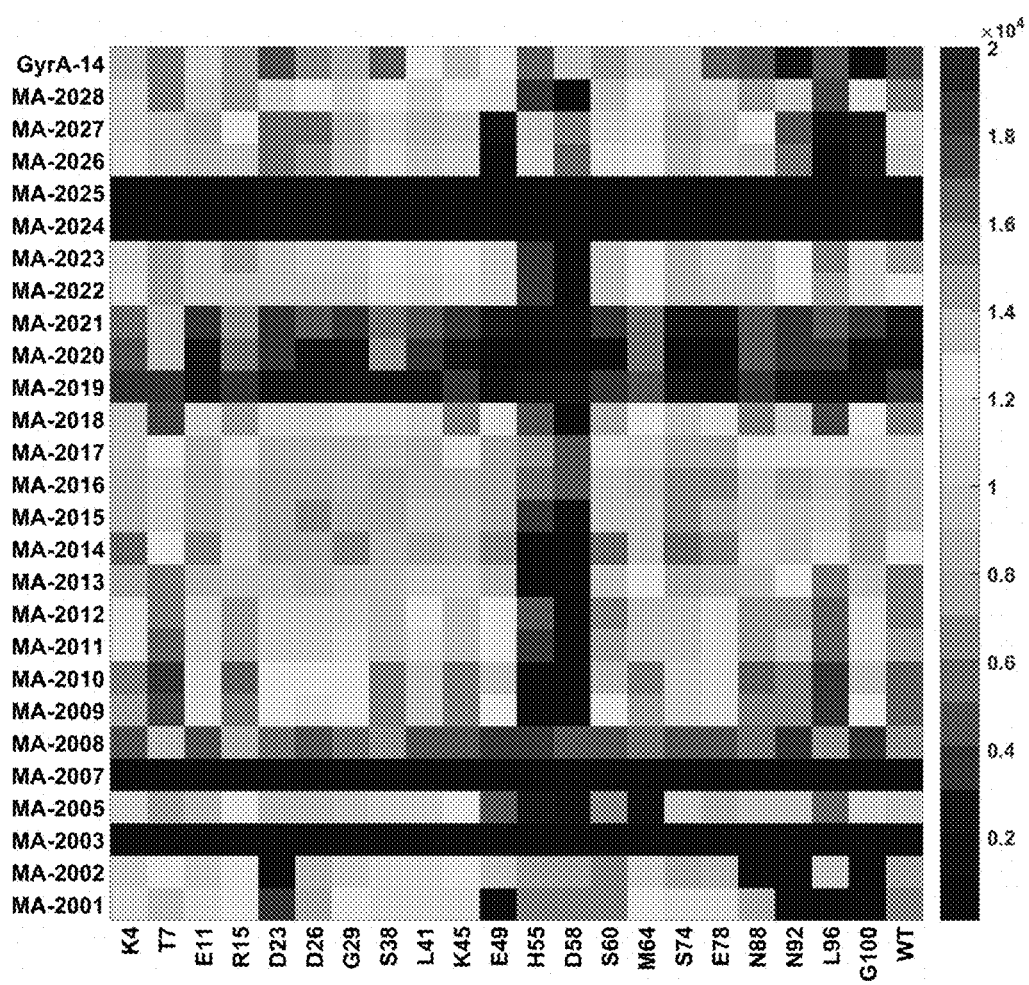
FIG. 2 depicts the heat map summarizing the binding data for GyrA-14 and 26 mouse mAbs to a panel of 21 chemically masked single cysteine mutants by flow cytometry, in accordance with an embodiment of the present disclosure.

GyrA-14 was found to bind with similar affinity to all the displayed cysteine mutants (FIG. 2), except N92 and G100 which are part of the GyrA-14 binding site (Dao-Thi et al., 2005). This indicated that the selected cysteine mutations do not perturb the overall conformation of the displayed protein. This result was consistent with previous studies (Adkar et al., 2012; Bajaj et al., 2005) where it was shown that mutation of non-active site, surface exposed residues (residues having accessibility ≥30%) does not perturb the secondary structural elements, the protein remains in its dimeric form, and is fully active (Bajaj et al., 2008).

Example 3

Labeling of Displayed Cysteine Mutants and MAb Binding by Flow Cytometry:

All the cysteine mutants were labeled individually with biotin-PEG2-maleimide (Thermo Scientific), prior to probing with MAbs or GyrA-14 for epitope mapping. The MAbs were developed in the laboratory against CcdB and each of these MAbs were randomly named as MA-2001 . . . to MA-2026. In brief, $1 \times 10^6$ induced yeast cells from each cysteine mutant, after being washed thrice with 1×PBS pH 8.0, were individually incubated with 5 mM biotin-PEG2-maleimide in 1×PBS pH: 8.0 at 4° C. for 4 h on a Rotospin to facilitate efficient labeling. The labeled cells were then washed 5-6 times with ice cold 1×PBS to remove unbound label. For labeling under denaturing conditions, $10^6$ cells were incubated with 5 mM biotin-PEG2-maleimide in the presence of 2M Gdn-HCl for 2 hours at room temperature. Cells were washed thrice with 1×PBS followed by probing with GyrA-14 or MAbs as described previously.

To determine binding specificity, the labeled cells from each individual mutant were incubated with each of the 26 MAbs separately at 25 nM final concentration or 100 nM of FLAG-tagged GyrA-14 in a final volume of 50 µL in ice cold PBSB for 3 h at 4° C. Cells stained with GyrA-14 were further probed with anti-FLAG tag antibody (Sigma Aldrich Inc.). After washing thrice with ice cold PBSB buffer, the cells were subsequently stained with Alexa Fluor-633 goat anti-mouse antibody (Life Technologies) at a pre-determined dilution 1:500 in PBSB for 1 h at 4° C. Cells were washed thrice with ice cold PBSB and subjected to flow cytometry (Accuri C6 flow cytometer, BD Biosciences). The data was analyzed using BD CSampler Software (BD Biosciences).

Masking of the cysteine residue/residues in the vicinity of the GyrA-14 binding site was predicted to prevent GyrA-14 from binding to the antigen (CcdB) and this loss in binding is evidenced in FIG. 3. Partial to complete loss in binding was observed when residues at position 26, 88, 96 and 23, 92, 100 respectively on CcdB were mutated to cysteine and subsequently masked by labeling with biotin-PEG2-maleimide (FIG. 3 *a-d*). When the results were compared with the crystal structure of CcdB-GyrA complex, the interacting residues were predicted with very high accuracy thus validating the method. When compared with mutational phenotypes derived from saturation mutagenesis of CcdB (Adkar et al., 2012) (FIG. 3*d*), it can be seen that several binding site residues that are relatively tolerant to mutation to other amino acids (>50% mutations tolerated) are sensitive to Cys labeling, highlighting the advantage of the present approach for epitope mapping (FIG. 2, FIG. 3).

Next, in a similar manner, the binding of 26 MAbs were mapped to the displayed single cysteine mutants individually. As an example, the MAb, MA-2001 lost binding when residues at each of the positions 49, 92, 96 and 100 were mutated to cysteine and subsequently masked by labeling with biotin-PEG2-maleimide. Only partial binding was observed when residues 23 and 26 were mutated and labeled (FIG. 2). These residues are in close proximity in the three-dimensional structure, forming a discontinuous conformational epitope (FIG. 3*e*). It was found that all the tested MAbs target the same epitope on the antigen from residues 55-58, which is a continuous stretch of amino acids (FIG. 2, FIG. 3*g*).

Example 4

Cysteine Mutant Library Construction and Sorting of Bound/Unbound Clones by FACS:

In order to construct the surface display library, cells expressing each of the cysteine mutants were pooled in equal proportion to construct a library representing all the cysteine mutants. Briefly, a single colony from each cysteine mutant was inoculated in a test-tube individually and grown overnight. The next day, an equal number of cells from each mutant were pooled and inoculated in a single flask of SDCAA medium in such a way that the final $OD_{600}$ of the mixed culture is less than 0.5. Pooled culture was grown at 30° C. till an $OD_{600}$ of 3-4, followed by induction in SGCAA medium at 20° C. for 24 h. A total of $4\times10^6$ cells of this library were labeled with biotin-PEG2-maleimide, as described earlier.

For sorting labeled cells, a dual-labeling strategy was used, wherein surface expression (anti-HA tag antibody) and ligand (MAb or GyrA-14) binding were individually probed with appropriately labeled secondary antibodies. This dual labeling was important for normalizing the binding signal to the expression level and to separate out the non-expressing cells. Labeled cells probed with only anti-HA antibody (anti-$HA^+$) were also sorted to determine relative expression levels of individual mutants in the pool (FIG. 4*f*).

The probing strategy used was as follows, the pooled cultures of cysteine mutants were divided into six aliquots. Each of the six aliquots were probed, respectively, with MAb, MA-2001 and anti-HA antibody (FIG. 4*a*), the second aliquot was probed with MA-2002 and anti-HA antibody (FIG. 4*b*), the third aliquot was probed with MA-2010 and anti-HA antibody (FIG. 4*d*), the fourth one with MA-2018 and anti-HA antibody (FIG. 4*e*), fifth one with FLAG-tagged GyrA-14 and anti-HA antibody (FIG. 4*c*) and the sixth one with anti-HA antibody alone (FIG. 4*f*). All six aliquots were probed separately with respective MAbs (25 nM) and GyrA-14 plus anti-HA antibody (1:250 dilution) in a final volume of 50 μL at 4° C. for 1 h. The cells were washed thrice with ice cold PBSB buffer and subsequently stained with Alexa Fluor-633 goat anti-mouse (1:500 dilution) plus Alexa Fluor-488 goat anti-chicken (1:250 dilution) for 1 h at 4° C. in the dark. After washing thrice with ice cold PBSB buffer, cells were resuspended in 500 μL PBSB buffer, subjected to flow cytometry and sorted on an Aria-III cell sorter (BD Biosciences). Cells were sorted at a flow rate of 3,000 events $s^{-1}$ in purity mode. Ten thousand cells were collected from each aliquot separately and plated onto SDCAA agar plates. Data was analyzed using BD FACSDiva software (BD Biosciences) (FIG. 4 *a-f*).

After sorting, plasmids were extracted from the sorted cells, the CcdB gene in the plasmid pool was PCR amplified and subjected to deep sequencing in an Illumina MiSeq machine. In a separate experiment, individual clones were also recovered after transformation into *E. coli* and sequenced by Sanger sequencing. The results from both Sanger sequencing and deep sequencing, were quite consistent with data obtained from screening of individual cysteine mutants by yeast display (FIG. 4*g, h*)

Example 5

DNA Sequencing of the Sorted Clones:

For DNA sequencing, sorted yeast cells from each aliquot were grown separately in liquid SDCAA medium to saturation at 30° C. for 20 h and plasmids were extracted by Phenol:Chloroform:Isoamylalcohol mixture as described previously (Hoffman and Winston, 1987). The plasmids were then transformed into *E. coli* DH5α cells and 96 clones from each aliquot were sequenced by Sanger sequencing (Macrogen Inc.).

Example 6

Deep Sequencing of Sorted Population:

For deep sequencing, sorted yeast cells from each aliquot were grown separately in liquid SDCAA medium to saturation at 30° C. for 20 h, and pooled plasmids were extracted using EZ Yeast™ plasmid miniprep kit (G Biosciences) according to the manufacturer's instructions and subjected to PCR as described below.

The expected maximum read length that can be obtained using Illumina sequencing with the MiSeq platform is 300 bases from each end in a paired end read (2×300). Flanking primers with Multiplex IDentifier (MID) tags were designed so that the amplified product covers the entire sequence of the CcdB gene (306 bases)(Adkar et al., 2012). The design of the PCR primer is such that for the forward end read, the first 3 bases are NNN followed by 6 bases of unique sequence tag (MID) and the 21 bases of the primer sequence complementary to the gene. Each MID sequence represents a particular MAb, GyrA-14 or anti-HA antibody.

The PCR for all the pooled plasmids from six sorted samples (MA-2001⁻, MA-2002⁻, MA-2010⁺, MA-2018⁺, GyrA-14 and HA⁺) was carried using Phusion polymerase with a high template concentration (10 ng/μL) for 10 cycles. The PCR was carried out in a 100 μL reaction volume for each sample. Following agarose gel electrophoresis, the concentration was quantified using BioRad Quantity One software (BioRad) and an equal amount (~500 ng) of PCR product from each sample was mixed and then gel-band purified, followed by sequencing on the MiSeq platform. The PCR products were pooled with several other PCR products from unrelated experiments. The CcdB PCR products derived above represented ~1% of the total DNA subjected to deep sequencing.

For processing the deep sequencing data, the raw reads were first segregated into bins based on their MID tag. Primer sequence was used to identify forward and reverse reads in each bin. The reads were filtered using a Phred score cutoff of 20. Minimum read length cutoff of 75 was employed and reads were converted into FASTA format and then aligned with full length gene sequence using the WATER program of the EMBOSS package (Carver and Bleasby, 2003; Rice et al., 2000). All parameters were kept at default values except the Gap Opening Penalty, which was increased to 20. The XY coordinate information was used to ensure that the combined information from forward and reverse reads had only a unique single mutation. Reads with single Cys mutants were identified using the alignment output and frequencies of occurrence of the mutants were set to be equal to the number of reads for each mutant in a given sorted population.

The number of reads for each mutant obtained from anti-HA antibody sorted cells (typically about 1000) was used to estimate the total population of each mutant independent of its ability to bind MAb or GyrA-14. The number of reads for each mutant in the bound (+) was hence normalized as follows:

$$\frac{\text{\# of reads (+)}}{\text{\# of reads (HA)}} \times 1000$$

A similar normalization was done for the unbound (−) populations.

Example 7

Binding of Rabbit Polyclonal Sera to Single Cysteine Mutants Probed by Flow Cytometry:

The two regions that act as the immunodominant regions or antigenic sites on the CcdB protein are the active site of the antigen, which is involved in binding to its ligands gyrase and CcdA protein and, secondly towards an exposed, continuous stretch of amino acids from residues 55-58. To test whether these regions are also immunodominant in another animal model, polyclonal sera were obtained by immunizing rabbits with the same antigen.

To map the immunodominant regions on antigen (CcdB), the labeled cell surface displayed individual mutants were incubated with 1:20,000 dilutions (FIG. 6) of rabbit polyclonal sera to a final volume of 50 μL in ice cold PBSB for 3 h at 4° C. After washing thrice with ice cold PBSB buffer, cells were subsequently stained with Alexa Fluor-633 mouse anti-rabbit antibody (Life Technologies) at a pre-determined dilution of 1:500 in PBSB for 1 h at 4° C. Cells were washed thrice with ice cold PBSB and subjected to flow cytometry (Accuri C6 flow cytometer, BD Biosciences). The data was analyzed using BD CS ampler Software (BD Biosciences).

As shown (FIG. 5a, b) most of the immune response appears to be generated towards either the Gyrase binding site or the 55-58 loop region in rabbits thus confirming that these two regions are the immunodominant regions of CcdB protein in two different animal models. Similar results were observed when we determined the binding of polyclonal sera to overlapping peptides of the antigen (FIG. 5c, d).

To further confirm this, competitive binding studies of rabbit polyclonal antibodies with mouse MAbs and GyrA-14, by ELISA were conducted. Rabbit polyclonal sera competed strongly with mouse MAbs (MA-2001, -2002, -2026, -2027) as well as with GyrA-14. However, no or very little competition was observed with MAbs MA-2010, -2012 suggesting that 55-58 loop binding antibodies are the minor component of the polyclonal sera (FIG. 13).

Epitope Mapping in the Presence of Denaturant:

In order to demonstrate that cysteine labeling occurred only for surface exposed residues, V18 (accessibility 0% and depth 10 Å) was mutated to cysteine, displayed on the yeast surface labeling was confirmed by monitoring binding to GyrA-14 by flow cytometry. Labeling was also carried out in the presence and absence of denaturant. It is expected that once the buried residue V18C is labeled, the protein will no longer be able to bind GyrA-14. In the absence of denaturant there was no loss of binding for labeling times as long as 24 hours. In contrast, for labeling in the presence of denaturant there was complete loss of binding even at the first time point of 5 minutes. The negative control, wild-type CcdB, lacking any Cys residue, or R15C mutant with an exposed Cys away from the GyrA-14 binding site, showed no loss of binding after incubation with the labeling reagent either in the presence or absence of denaturant (FIG. 8,9,10).

Figure 11:
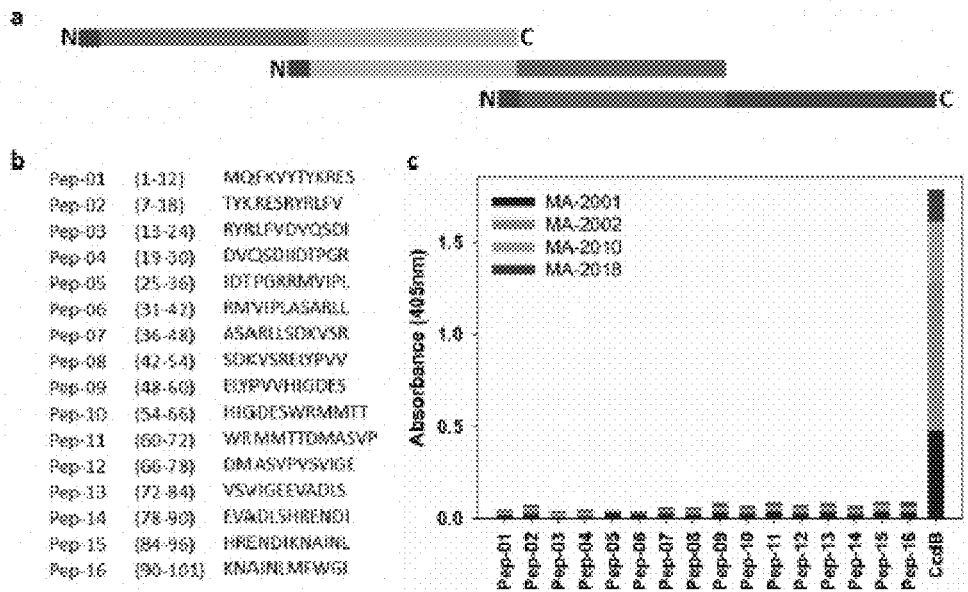

Epitope Mapping Using Linear Peptides:

To compare the instant method with conventional epitope mapping using overlapping peptides, a set of overlapping peptides were designed to cover the entire sequence of the antigen. Sixteen, 12-mer overlapping biotinylated peptides with an overlap of 6 amino acids that spanned the entire length of the CcdB were synthesized and the binding of the MAbs (MA-2001, -2002, -2010, and -2018) were determined by ELISA. As expected, MA-2001 and -2002 did not bind to any of the overlapping peptides, confirming that these MAbs bind to discontinuous conformational epitopes. Surprisingly, MA-2010 and -2018 also did not bind to the overlapping peptides likely because of the lack of either conformational specificity or the presence of other residues in the epitope. These results also illustrate the advantages of the disclosed method relative to epitope mapping with linear peptides (FIG. 11).

Competitive Binding of MAbs with GyrA-14 and CcdA$_{50-72}$ Peptide:

In order to assess the binding behaviours of GyrA-14 or CcdA$_{50-72}$ to the antigen to the CcdB protein, the ProteOn XPR36 protein interaction array system was used for competitive binding studies. Recombinant purified CcdB was immobilized onto the GLC sensor chip by amine coupling chemistry and binding of GyrA-14 or CcdA$_{50-72}$ to the immobilized antigen was monitored in the presence and absence of MAbs. To shield the GyrA-14 or CcdA$_{50-72}$ binding surface, MAbs were first passed over the immobilized antigen to form an antigen-antibody complex followed by GyrA-14 or CcdA$_{50-72}$ peptide. The results indicate that MA-2001 greatly interferes with the GyrA-14 as well as CcdA$_{50-72}$ peptide binding, hence, its epitope completely overlaps with the GyrA-14 and CcdA$_{50-72}$ peptide binding sites. Although, MA-2002 interferes with the binding of GyrA-14, it has no effect on the binding of CcdA$_{50-72}$ peptide, hence the epitope of this antibody does not overlap with the CcdA$_{50-72}$ peptide binding site, indicating that this antibody approaches the antigen at a different angle than MA-2001 (FIG. 11, 12). However, other antibodies whose epitopes mapped to regions outside the GyrA-14 or CcdA peptide binding sites do not interfere with their binding as expected. These data further validate the proposed epitope mapping approach.

Example 8

Cysteine Scanning Mutagenesis to Map HIV-1 Env:Antibody Binding Sites and Conformational Epitopes in the HIV-1 Virus The objective of the present example is to develop a simple and efficient method for accurate localization of both conformational as well as linear antibody epitopes on the HIV-1 envelope glycoprotein (Env). This is carried out by generation of a library of engineered single cysteine mutations at various exposed positions in the HIV-1 virus.

This is followed by labelling the mutant viruses with a cysteine-reactive biotin derivative (Maleimide-PEG2-Biotin). The cysteine label reacts with exposed cysteines on Env, thereby masking the epitopes. Further, because of the steric bulk of the masking reagent, it is anticipated that labelling of virtually all epitope residues will result in loss of antibody binding and in addition, buried residues will be inaccessible to the labelling reagent, except in the case of dynamically flexible regions. The epitope or binding site can be subsequently deciphered by deep sequencing of the pooled library of exposed positions in the native HIV-1 Env (FIG. 14).

For generation of the exposed Cys library, 83 exposed residues were selected in the HIV-1 from the Protein Data Bank entry 4TVP using a combined criterion of >30% surface accessibility and sidechain-sidechain centroid distance >8 Å. Most of the selected exposed residues form part of the epitope of the various broadly neutralizing antibodies and are contact residues for the primary receptor CD4.

Protein Labelling: Proteins used for labelling had a concentration between 1-10 mg/ml, to this 100-fold molar excess of TCEP (Tris-carboxyethylphosphine) reagent was added to reduce disulfide bonds. This mixture was kept at 20 minutes at room temperature. To this, 20-fold molar excess of the cysteine label was added, and the reaction was quenched by addition of 0.5% of DTT to the reaction mixture and incubating at 10 minutes at room temperature. Virus stocks are stored in growth media DMEM which is supplemented with 20% Fetal Bovine Serum (FBS) which itself has a protein content of 30-40 mg/ml, because of which, high concentrations of the cysteine label (Biotin-PEG$_2$-Maleimide) are required for efficiently labelling the virus.

To decide the amount of the cysteine label to use for subsequent experiments, a test protein, Gyrase with a free cysteine mutant (GyrA14 I491C) in 20% FBS was passed through a CcdB bound column and the extent of cysteine labelling was quantified using mass spectrometry (MALDI), at different concentrations of label and at different time points. It was found that 10 mM Label and overnight incubation leads to maximum label incorporation and therefore the same conditions were used to label the virus. The infectivity of the wild-type virus (300000 RLU equivalents) post labelling with 10 mM reagent was checked using TZM-bl cells. It was found that infectivity is retained post labelling, and infectivity is somewhat higher is cases where labelling is quenched with the addition of DTT.

This labelling methodology was subsequently extended to the exposed cysteine libraries of the HIV-1 Env. The Complete_Cys_Library consists of all the cysteine mutants whereas the Exposed_Cys_Library consists of only the exposed cysteine mutants. Viral infectivity follows the order Exposed_Cys_Library>Complete_Cys_Library>wild-type.

Epitope mapping: Proof of principle epitope mapping was carried out using the T278C mutant virus. T278 is a known contact residue for the broadly neutralizing antibody VRC01. For the wild-type virus, the IC$_{50}$ with VRC01 was determined to be about 40 ng/ml. Therefore, the present example used VRC01 concentrations far higher than the IC$_{50}$ for subsequent experiments.

The T278C mutant virus was labelled and infectivity was checked under the following conditions: (i) labelled, followed by VRC01 incubation, (ii) no label, VRC01, (iii) label, no VRC01 and (iv) no label, no VRC01.

For these experiments, 5 µg/ml of VRC01 was used which was far higher than the determined IC$_{50}$. It was found that upon labelling, the T278C mutant virus becomes resistant to neutralization by VRC01 (FIG. 15) validating the fact that it is part of the VRC01 epitope. The decrease in infectivity of the T278C upon labelling could be attributed to the fact that T278 is in close proximity to the CD4 binding site, and the infectivity decrease could occur as a result of steric occlusion by the bulky label.

Example 9

Cysteine Scanning Mutagenesis to Find Interacting Residues Between MazE and MazF of *Mycobacterium tuberculosis* TA Systems The present example depicts the utility of cysteine scanning mutagenesis to find interacting residues between MazE and MazF of *Mycobacterium tuberculosis* TA systems. MazE and MazF are interacting partners in Toxin/Anti-toxin system of *Mycobacterium tuberculosis*. The detailed methodology is similar to the one used for CcdB antigen as described previously in the present document.

The present example describes steps of a simple and efficient method for accurate mapping of protein-protein interaction of the MazEF3, MazEF6, MazEF9 TA systems of *Mycobacterium tuberculosis*. This method involves screening a panel of purified cognate proteins or peptides (toxin/antitoxin) against a panel of chemically masked single cysteine mutants of its interacting partner displayed on the surface of yeast cells. Such libraries would have much lower diversity than those generated by saturation mutagenesis, simplifying library generation and data analysis. Further, because of the steric bulk of the masking reagent, labelling of virtually all exposed epitope residues will result in loss of binding and buried residues will be inaccessible to the labelling reagent. The binding residues are deciphered by probing the loss of binding of labelled surface displayed protein with its cognate partner by flow cytometry.

Referring to FIG. 16, as a proof of principle, yeast cells displaying MazE3 (top) or MazF3 (bottom) were incubated with fluorescent antibodies to monitor the surface expression of the displayed protein (AlexaFluor-488, left) and ligand binding (AlexaFluor-633, right). A and B show histograms of the uninduced (grey) cells i.e. yeast cells not induced with galactose, unlabelled (before Cys labeling) MazE3 and MazF3 (blue) and labelled (after Cys labeling) MazE3 and MazF3 (red). The observed fluorescence for un-induced cells is due to auto-fluorescence of the cells. Labelled MazE3 and MazF3 cells showed similar expression, however the binding was higher as compared to the unlabelled cells. The decreased binding in the labelled cells indicates that at least one of the cysteine residues (C62 or C71 in wild-type MazF3 and C98 in wild-type MazE3) are involved in interaction with the cognate partner.

Advantages of the Present Disclosure

Overall, the present disclosure provides a rapid and reliable method for identifying specific epitopes on a protein of interest by using cysteine labelling. The method as described herein specifically depicts advantages of the method to identify binding regions on a variety of proteins such as CcdB, HIV-1 envelope glycoprotein (Env), and *Mycobacterium tuberculosis* TA systems. The method as described in the present disclosure can be employed for preparation of surface display libraries for yeast cells, mammalian cells, phage and lentivirus.

We claim:

1. A method of identifying binding sites of a molecule of interest on a receptor protein, said method comprising:
   a. obtaining a display population, wherein said population comprises cells, phage or virus, each member expressing on its surface a single mutant variant of the receptor protein, wherein said mutant variant has a single amino acid residue mutated to cysteine;
   b. contacting a cysteine specific probe with said population, wherein said cysteine specific probe binds to cysteine residue on mutant variant;
   c. contacting said molecule of interest with the display population; and
   d. detecting binding of molecule of interest to mutant variant of receptor protein,
   wherein lack of binding of molecule of interest to the mutant variant is indicative that the corresponding amino acid residue in the non-mutated receptor protein at the same position is involved in molecule of interest binding to receptor protein.

2. The method as claimed in claim 1, wherein said receptor protein has no cysteine residues, and said mutant variant has a single mutation, wherein said mutation is a substituted cysteine.

3. The method as claimed in claim 1, wherein said receptor protein has "n" number of cysteine residues involved in binding of molecule of interest, and in said mutant variant, the "n" number of cysteine residues of the receptor protein are substituted with alanine or serine or any other amino acid, and further, an additional single substitution to cysteine is made at an amino acid position which is not any of the "n" number of cysteine residues in the receptor protein.

4. The method as claimed in claim 3, wherein "n" can be 1 or greater than 1.

5. The method as claimed in claim 1, wherein in said population, each cell expresses the same mutant variant of the receptor protein.

6. The method as claimed in claim 1, wherein said population comprises two or more sub-populations, wherein each sub-population comprises yeast cells expressing a unique mutant variant.

7. The method as claimed in claim 1, wherein said mutant variant is tethered to the cell surface.

8. The method as claimed in claim 1, wherein said cysteine specific probe is selected from the group consisting of Biotin-maleimide, Biotin-PEG2-maleimide, Biotin-PEG11-maleimide, Iodoacetic acid, Methyl methanethiosulfonate, Iodoacetamide, N-Methoxycarbonylmaleimide, Methoxy PEG Maleimide, Ellmans reagent (DTNB), TAMRA maleimide, N-(5-Fluoresceinyl)maleimide, Alexa-maleimides, Tetramethylrhodamine-maleimide, Cyanine maleimide, N-(1-Pyrenyl)maleimide, and Sulfo-Cyanine maleimide and methane thiosulfonate derivatives.

9. The method as claimed in claim 1, wherein said cysteine specific probe binds to surface exposed cysteine residues.

10. The method as claimed in claim 1, wherein said cysteine specific probe binds to non-exposed cysteine residues in presence of a denaturant.

11. The method as claimed in claim 1, wherein said molecule of interest is selected from the group consisting of antibody or fragments thereof, DNA, RNA, chemical molecule, biological molecule, peptide, polypeptide, and combinations thereof.

12. The method as claimed in claim 1, wherein said display population is selected from the group consisting of yeast display library, phage display library, mammalian display library, and lentiviral display library.

13. The method as claimed in claim 12, wherein said yeast, phage, mammalian display library, or lentiviral display population is prepared by:
   a. obtaining a receptor protein;
   b. creating a population of receptor protein mutant variants, wherein each mutant variant contains a single amino acid residue mutated to a cysteine; and
   c. tethering mutant variants to yeast cell, mammalian cell, phage or lentivirus surface to obtain a surface display population.

14. The method as claimed in claim 7, wherein said population comprises yeast cells with a single type of mutant variant tethered to the cell surface.

15. The method as claimed in claim 7, wherein said population comprises at least two sub-populations, wherein each subpopulation comprises yeast cells with a single type of mutant variants tethered to yeast cell surface.

16. The method as claimed in claim 1, wherein the receptor protein is selected from the group consisting of CcdB antigen, HIV-1, and TA (toxin/anti-toxin) systems of *Mycobacterium tuberculosis*.

17. The method as claimed in claim 16, wherein the receptor protein is selected from the group consisting of HIV-1 Env, MazE3, MazEF6, and MazEF9.

* * * * *